(12) United States Patent
Nandimandalam et al.

(10) Patent No.: US 9,878,209 B2
(45) Date of Patent: Jan. 30, 2018

(54) FACILITATING DYNAMIC MONITORING OF BODY DIMENSIONS OVER PERIODS OF TIME BASED ON THREE-DIMENSIONAL DEPTH AND DISPARITY

(71) Applicant: INTEL CORPORATION, Santa Clara, CA (US)

(72) Inventors: Venkata Siva Varun Kumar Nandimandalam, Bonham, TX (US); Jim Santiago Baca, Corrales, NM (US); Neal P. Smith, Folsom, CA (US); David W. Baker, Chandler, AZ (US)

(73) Assignee: INTEL CORPORATION, Santa Clara, CA (US)

( * ) Notice: Subject to any disclaimer, the term of this patent is extended or adjusted under 35 U.S.C. 154(b) by 124 days.

(21) Appl. No.: 14/864,764

(22) Filed: Sep. 24, 2015

(65) Prior Publication Data

US 2017/0087415 A1  Mar. 30, 2017

(51) Int. Cl.
*A63B 24/00* (2006.01)
*G06K 9/00* (2006.01)
(Continued)

(52) U.S. Cl.
CPC ......... *A63B 24/0075* (2013.01); *A41H 3/00* (2013.01); *A61B 5/00* (2013.01); *G06K 9/00214* (2013.01);
(Continued)

(58) Field of Classification Search
CPC ........ A63B 24/0075; A41H 3/00; A61B 5/00; G06T 7/50; G06T 5/50; G06T 7/00;
(Continued)

(56) References Cited

U.S. PATENT DOCUMENTS

| 7,328,119 B1 | 2/2008 | Pryor et al. | |
| 2003/0108851 A1* | 6/2003 | Posa | G09B 19/0076 434/238 |

(Continued)

OTHER PUBLICATIONS

Notification of Transmittal of the International Search Report and the Written Opinion of the International Searching Authority issued for International Patent Application No. PCT/US2016/044508, dated Nov. 3, 2016.

*Primary Examiner* — Jon Chang
(74) *Attorney, Agent, or Firm* — Blakely, Sokoloff, Taylor & Zafman LLP

(57) ABSTRACT

A mechanism is described for facilitating smart monitoring of body dimensions according to one embodiment. A method of embodiments, as described herein, includes receiving a first request to take a first picture of a user, wherein the first picture is taken at a first point in time using a depth-sensing camera; automatically computing first body dimensions relating to a body of the user based on at least one of a first image of the body and first depth information relating to one or more parts of the body, wherein the first image and the first depth information are obtained from the first picture; generate a first three-dimensional (3D) model of the body based on the first body dimensions; and communicating at least one of the first 3D model and the first body dimensions to a display device, wherein the display device to display at least one of the first 3D model and the first body dimensions.

19 Claims, 7 Drawing Sheets

(51) Int. Cl.
  *G06T 17/00*   (2006.01)
  *G06T 5/50*    (2006.01)
  *G06T 7/00*    (2017.01)
  *G09B 19/00*   (2006.01)
  *G06T 7/50*    (2017.01)
  *A41H 3/00*    (2006.01)
  *A61B 5/00*    (2006.01)

(52) U.S. Cl.
  CPC .................. *G06T 5/50* (2013.01); *G06T 7/00* (2013.01); *G06T 7/50* (2017.01); *G06T 17/00* (2013.01); *G09B 19/0092* (2013.01); *G06T 2207/10021* (2013.01); *G06T 2207/10028* (2013.01); *G06T 2207/20221* (2013.01)

(58) Field of Classification Search
  CPC ........... G06T 17/00; G06T 2207/10021; G06T 2207/10028; G06T 2207/20221; G06K 9/00214; G09B 19/0092
  See application file for complete search history.

(56) References Cited

U.S. PATENT DOCUMENTS

| | | |
|---|---|---|
| 2010/0312143 A1 | 12/2010 | Kim |
| 2011/0143322 A1 | 6/2011 | Tsang |
| 2014/0115052 A1 | 4/2014 | Silberstein et al. |
| 2014/0340479 A1 | 11/2014 | Moore et al. |
| 2015/0037771 A1* | 2/2015 | Kaleal, III ............... G09B 5/02 434/257 |
| 2016/0012646 A1* | 1/2016 | Huang .................... G06T 5/005 345/419 |

* cited by examiner

FACILITATING DYNAMIC MONITORING OF BODY DIMENSIONS OVER PERIODS OF TIME BASED ON THREE-DIMENSIONAL DEPTH AND DISPARITY

FIELD

Embodiments described herein generally relate to computers. More particularly, embodiments relate to facilitating dynamic monitoring of body dimensions over periods of time based on three-dimensional depth and disparity.

BACKGROUND

Conventional techniques involve physical measuring tapes for measuring human body dimensions. Such techniques require a user to manually measure dimensions of a human body using a measuring tape, which is time-consuming, cumbersome, inefficient, and prone to human errors.

BRIEF DESCRIPTION OF THE DRAWINGS

Embodiments are illustrated by way of example, and not by way of limitation, in the figures of the accompanying drawings in which like reference numerals refer to similar elements.

DETAILED DESCRIPTION

Figure 1:
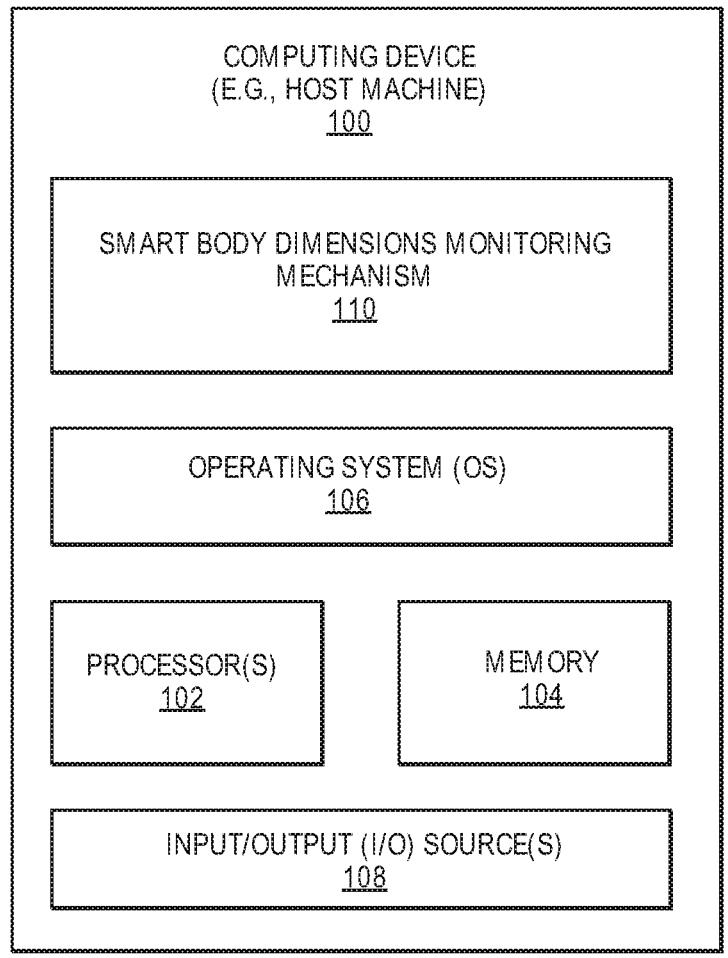
FIG. 1 illustrates a computing device employing a smart body dimensions monitoring mechanism according to one embodiment.

In the following description, numerous specific details are set forth. However, embodiments, as described herein, may be practiced without these specific details. In other instances, well-known circuits, structures and techniques have not been shown in details in order not to obscure the understanding of this description.

Embodiments provide for a novel technique for generating three-dimensional (3D) models representing human body dimensions using one or more of depth sensors, depth-sensing cameras (e.g., Intel® RealSense™, etc.), ranging cameras, time-of-flight (ToF) cameras, etc. It is contemplated that body dimensions, as referenced throughout this document, may include measurements, forms, shapes, etc., of any number and type of body parts/areas, such as height of a person, width of a chest, circumference of a waist, length of an arm, etc. Further, in one embodiment, this process may be repeated over time to obtain multiple sets of dimensions, which may then be compared or matched against each other to track any changes in the person's body dimensions that may have occurred over a period of time.

This novel technique also allows for users to achieve their individual goals or targets relating to body dimensions, such as when engaging in a weight loss program, preparing for a sporting/social event, etc. For example, a 3D model based on a desired set of body dimensions may be generated by a user, where the model may then be used as a target model by the user to achieve the desired set of body dimensions. In some embodiment, a user interface may be provided for easy adjustment or modification of the target model by the user, as necessitated or desired. In one embodiment, multiple sets of dimensions may be stitched or merged together at various points in time for various reasons, such as for comparison purposes to view the before-and-after displays of the user's changing body dimensions.

As aforementioned, conventional techniques require a manual measurement of body dimensions using a measuring tape where the user is required to continuously manually measure various body areas, such as waist, chest, etc., and then store the values, and time and again, manually track the progress or lack-thereof by comparing the new values with one or more previous values over various points in time. Such and other conventional techniques are inefficient, inaccurate, time-consuming, and cumbersome.

Embodiments provide for a technique for employing a local/back-end analytics applied to depth images obtained over time using, for example, a depth-sensing camera, where the analytics are used over various points in time to show progress or lack-thereof for a user by showing how the user's body dimensions measure at a particular point in time compared to how the body dimensions were at any previous point in time or expect to be at any future point in time.

It is contemplated and to be noted that embodiments are not limited to any particular number and type of software applications, application services, customized settings, etc., or any particular number and type of computing devices, networks, deployment details, etc.; however, for the sake of brevity, clarity, and ease of understanding, throughout this document, references are made to body dimensions, measurements, tracking, progress, 3D models, user interfaces, software applications, user preferences, customized settings, mobile computers (e.g., smartphones, tablet computers, etc.), communication medium/network (e.g., cloud network, the Internet, proximity network, Bluetooth, etc.), but that embodiments are not limited as such.

Figure 2:
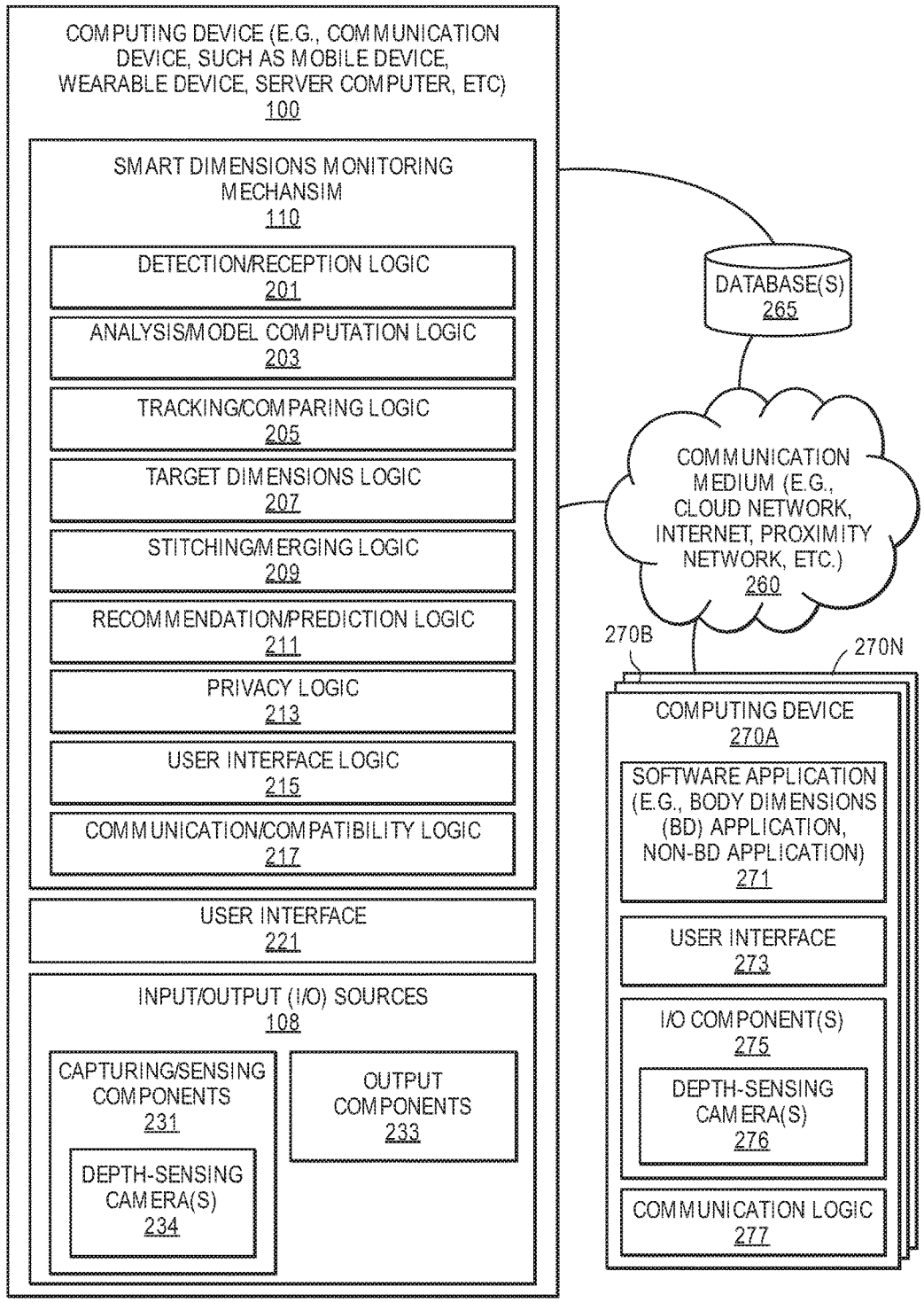
FIG. 2 illustrates a smart body dimensions monitoring mechanism according to one embodiment.

FIG. 1 illustrates a computing device 100 employing a smart body dimensions monitoring mechanism 110 according to one embodiment. Computing device 100 serves as a host machine for hosting smart body dimensions monitoring mechanism ("smart dimensions mechanism" or simply "dimensions mechanism") 110 that includes any number and type of components, as illustrated in FIG. 2, to facilitate dynamic and real-time monitoring, tracking, and analysis of body dimensions over various points in time, as will be further described throughout this document.

Computing device 100 may include any number and type of data processing devices, such as large computing systems, such as server computers, desktop computers, etc., and may further include set-top boxes (e.g., Internet-based cable television set-top boxes, etc.), global positioning system (GPS)-based devices, etc. Computing device 100 may include mobile computing devices serving as communication devices, such as cellular phones including smartphones, personal digital assistants (PDAs), tablet computers, laptop computers (e.g., Ultrabook™ system, etc.), e-readers, media internet devices (MIDs), media players, smart televisions, television platforms, intelligent devices, computing dust, media players, head-mounted displays (HMDs) (e.g., wearable glasses, such as Google® Glass™, head-mounted binoculars, gaming displays, military headwear, etc.), and other wearable devices (e.g., smartwatches, bracelets, smartcards, jewelry, clothing items, etc.), and/or the like.

Computing device 100 may include an operating system (OS) 106 serving as an interface between hardware and/or physical resources of the computer device 100 and a user. Computing device 100 further includes one or more processor(s) 102, memory devices 104, network devices, drivers, or the like, as well as input/output (I/O) sources 108, such as touchscreens, touch panels, touch pads, virtual or regular keyboards, virtual or regular mice, etc.

It is to be noted that terms like "node", "computing node", "server", "server device", "cloud computer", "cloud server", "cloud server computer", "machine", "host machine", "device", "computing device", "computer", "computing system", and the like, may be used interchangeably throughout this document. It is to be further noted that terms like "application", "software application", "program", "software program", "package", "software package", "code", "software code", and the like, may be used interchangeably throughout this document. Also, terms like "job", "input", "request", "message", and the like, may be used interchangeably throughout this document. It is contemplated that the term "user" may refer to an individual or a person or a group of individuals or persons using or having access to computing device 100.

FIG. 2 illustrates a smart body dimensions monitoring mechanism 110 according to one embodiment. In one embodiment, smart dimensions mechanism 110 may include any number and type of components, such as (without limitation): detection/reception logic 201; analysis/model computation logic 203; tracking/comparing logic 205; target dimensions logic 207; stitching/merging logic 209; recommendation/prediction logic 211; privacy logic 213; user interface logic 215; and communication/compatibility logic 217. Computing device 100 is further shown as providing user interface 221, as facilitated by user interface 215, and hosting input/output sources 108 having capturing/sensing components 231 and output sources 233, where capturing/sensing components 231 include depth-sensing camera(s) 232.

In one embodiment, smart dimensions mechanism 110 may be hosted by computing device 100, such as a communication/data processing device including a mobile computer (e.g., smartphone, tablet computer, etc.), a wearable computers (e.g., wearable glasses, smart bracelets, smartcards, smart watches, HMDs, etc.), an Internet of Things (IoT) devices, and/or the like. In another embodiment, computing device 100 may be a larger communication machine, such as a server computer, a desktop computer, a laptop computer, etc. In one embodiment, computing device 100 may be in communication with one or more computing devices (also referred to as "personal devices") 270A, 270B, 270N (e.g., mobile computer, such as a smartphone, a tablet computer, etc.) over communication medium 260, such as one or more networks (e.g., Cloud network, the Internet, proximity network, such as Bluetooth, etc.).

For example and in one embodiment, computing device 100 may serve as a server computer hosting smart dimensions mechanism 110 in its entirety while communicating one or more services offered by smart dimensions mechanism 110 with one or more personal devices, such as computing devices 270A-N, over communication medium 260, such as a cloud network. In another embodiment, computing device 100 itself may be another personal device, such as similar to or the same as one of computing devices 270A-N, where each computing device 100, 270A-N may include smart dimensions mechanism 110, either partially or entirely, as part or in support of a software application, such as software application (also referred to as "application" or "client-based application") 271. In one embodiment, software application 271 may include a body dimensions (BD) application or a non-BD application or any other type of software application, such as a web browser.

For example, in case of software application 271 being a non-BD application, a user having access to personal device 270A may use personal device 270A for any number and type of basic services and functionalities, such as having own body pictures taken at various points in time using depth-sensing camera 276 as provided by I/O components 275 of personal device 270A, etc., but rely on one or more components of smart dimensions mechanism 110 at computing device 100 for additional tasks, such as tracking, comparing, predicting, recommending, etc.

If, for example and in one embodiment, software application 271 is a BD application, which may be downloadable or accessible over communication medium 260 (e.g., cloud network), the BD application 271 may be the same as or similar to smart dimensions mechanism 110 such that various body dimensions monitoring-related tasks of smart dimensions mechanism 110 may be performed locally at computing device 270A using user interface 273 (e.g., mobile application interface, web browser, etc.).

In one embodiment, software application 271 may interact with smart dimensions mechanism 110 via communication logic 277 over communication medium 260 and further, in one embodiment, a user having access to computing device 270A may interact with software application 271 via user interface 273 (e.g., mobile application interface, web browser, etc.) and listen, play, and/or view contents, such as results, body dimensions, progress reports, tables, graphs, other audio and/or video contents, etc., through one or more I/O components 275, such as display screen/device, speakers, etc.

Computing device 100 may include I/O source(s) 108 including capturing/sensing components 231 and output components 233 which, as will be further described below, may also include any number and type of components, sensor arrays, detectors, displays, etc. For example, capturing/sensing components 231 may include (without limitation) two-dimensional (2D) cameras, three-dimensional (3D) cameras, sensor arrays, microphones, etc., while, output components 233 may include (without limitation) display screens, display/projection areas, projectors, speakers, etc. For example and in one embodiment, capturing/sensing components 231 may further include one or more depth-sensing cameras, such as Intel® RealSense™ camera, etc.

Computing devices 100, 270A-N may be further in communication with one or more repositories or data sources or databases, such as database(s) 265, to obtain, communicate, store, and maintain any amount and type of data (e.g., body dimensions, tracking data, user target data, 3D models, recommendations, predictions, data tables, data maps, media, metadata, templates, real-time data, historical contents, user and/or device identification tags and other information, resources, policies, criteria, rules, regulations, upgrades, etc.).

In some embodiments, communication medium 260 may include any number and type of communication channels or networks, such as cloud network, the Internet, intranet, Internet of Things ("IoT"), proximity network, such as Bluetooth, etc. It is contemplated that embodiments are not limited to any particular number or type of computing devices, services or resources, databases, networks, etc.

As with computing device 100, each of computing devices 270A-N may include I/O components 275, such as (without limitation) sensors, detectors, actuators, microphones, speakers, 2D/3D cameras, touchscreens, display devices, and/or the like. As with computing device 100, I/O components 275 may also include one or more depth-sensing cameras, such as Intel® RealSense™ camera, etc. For example, computing device 100 may include I/O sources 108 having any number and type of capturing/sensing components 231 (e.g., sensor array (such as context/context-aware sensors and environmental sensors, such as camera sensors, ambient light sensors, Red Green Blue (RGB) sensors, movement sensors, etc.), depth-sensing cameras, 2D cameras, 3D cameras, image sources, audio/video/signal detectors, microphones, eye/gaze-tracking systems, head-tracking systems, etc.) and output components 233 (e.g., audio/video/signal sources, display planes, display panels, display screens/devices, projectors, display/projection areas, speakers, etc.).

Capturing/sensing components 231 may further include one or more of vibration components, tactile components, conductance elements, biometric sensors, chemical detectors, signal detectors, electroencephalography, functional near-infrared spectroscopy, wave detectors, force sensors (e.g., accelerometers), illuminators, eye-tracking or gaze-tracking system, head-tracking system, etc., that may be used for capturing any amount and type of visual data, such as images (e.g., photos, videos, movies, audio/video streams, etc.), and non-visual data, such as audio streams or signals (e.g., sound, noise, vibration, ultrasound, etc.), radio waves (e.g., wireless signals, such as wireless signals having data, metadata, signs, etc.), chemical changes or properties (e.g., humidity, body temperature, etc.), biometric readings (e.g., figure prints, etc.), brainwaves, brain circulation, environmental/weather conditions, maps, etc. It is contemplated that "sensor" and "detector" may be referenced interchangeably throughout this document. It is further contemplated that one or more capturing/sensing components 231 may further include one or more of supporting or supplemental devices for capturing and/or sensing of data, such as illuminators (e.g., infrared (IR) illuminator), light fixtures, generators, sound blockers, etc.

It is further contemplated that in one embodiment, capturing/sensing components 231 may further include any number and type of context sensors (e.g., linear accelerometer) for sensing or detecting any number and type of contexts (e.g., estimating horizon, linear acceleration, etc., relating to a mobile computing device, etc.). For example, capturing/sensing components 231 may include any number and type of sensors, such as (without limitations): accelerometers (e.g., linear accelerometer to measure linear acceleration, etc.); inertial devices (e.g., inertial accelerometers, inertial gyroscopes, micro-electro-mechanical systems (MEMS) gyroscopes, inertial navigators, etc.); gravity gradiometers to study and measure variations in gravitation acceleration due to gravity, etc.

Further, for example, capturing/sensing components 231 may include (without limitations): audio/visual devices (e.g., cameras, microphones, speakers, etc.); context-aware sensors (e.g., temperature sensors, facial expression and feature measurement sensors working with one or more cameras of audio/visual devices, environment sensors (such as to sense background colors, lights, etc.), biometric sensors (such as to detect fingerprints, etc.), calendar maintenance and reading device), etc.; global positioning system (GPS) sensors; resource requestor; and trusted execution environment (TEE) logic. TEE logic may be employed separately or be part of resource requestor and/or an I/O subsystem, etc. Capturing/sensing components 231 may further include voice recognition devices, photo recognition devices, facial and other body recognition components, voice-to-text conversion components, etc.

Similarly, output components 233 may include dynamic tactile touch screens having tactile effectors as an example of presenting visualization of touch, where an embodiment of such may be ultrasonic generators that can send signals in space which, when reaching, for example, human fingers can cause tactile sensation or like feeling on the fingers. Further, for example and in one embodiment, output components 233 may include (without limitation) one or more of light sources, display devices and/or screens, audio speakers, tactile components, conductance elements, bone conducting speakers, olfactory or smell visual and/or non/visual presentation devices, haptic or touch visual and/or non-visual presentation devices, animation display devices, biometric display devices, X-ray display devices, high-resolution displays, high-dynamic range displays, multi-view displays, and head-mounted displays (HMDs) for at least one of virtual reality (VR) and augmented reality (AR), etc.

As previously described, embodiments provide for obtaining body dimensions using depth/disparity information based on pictures obtained through one or more depth-sensing cameras so that any dimensions-related results, such as tracking results, making predictions, offering recommendations, etc., are accurate, precise, timely, and efficient. In one embodiment, a 3D body model may be extracted from depth/disparity information obtained using a depth-sensing camera.

It is contemplated that embodiment are not limited to any particular number or type of use case scenarios; however, one or more use-case scenarios may be discussed throughout this document for the sake of brevity, clarity, and ease of understanding but it is to be noted that embodiments are not limited as such. For example, one or more use-case scenarios based on smart dimensions mechanism 110 may include (without limitations) 1) performing a one-time measurements of his/her body dimensions; or 2) obtaining multiple sets of measurements of body dimensions over a period of time where these multiple sets may be used to track the changes in the user's body dimensions, such as to determine progress or lack-thereof in terms of workout results, weight-loss expectations, etc. For example, a person who workout can take various pictures/3D of his/her body at regular intervals and then compare the results so that the person may track and know which parts of the body are making progress (e.g., biceps have increased by an amount, while waist dimensions have remained the same or gotten worse, etc.) and whether additional or different workout training pattern or sessions might be needed.

Similarly, other use-case scenarios based on smart dimensions mechanism 110 may include (without limitations): 3) taking an initial depth picture/3D model/mesh of himself/herself using a depth-sensing camera and then choose to adjust the 3D model, such as via user interface 221 at computing device 100, and use the adjusted 3D model a target dimensions to achieve in a certain amount of time (e.g., loose 2 inches of waist over 3 months or 50 pounds of overall weight in 6 months, etc.); or 4) continuing to obtain new body dimensions at various points in time to determine how close the person has reached to the target dimensions or even re-adjust the target model for setting a better target or a more realistic goal.

Similarly, other use-case scenarios based on smart dimensions mechanism 110 may include (without limitations): 5) combining multiple image obtained over time using one or more depth sensing cameras and stitch (also referred to as "merge") them into a single image which may then be reviewed by the user or other relevant individuals, such as the user's physical trainer, physician, team coach, etc., to see and analyze the user's progress with regard to the user's body dimensions over time. As aforementioned, the user may choose to share the stitched image and/or the multiple images with various professionals (e.g., physical trainer, doctor, team coach, etc.), family members, friends, etc., over communication medium 260.

Additional use-case scenarios based on smart dimensions mechanism 110 may include (without limitations): 6) tracking a user's goals and the progress in reaching these goals and based on the data obtained from tracking, smart dimensions mechanism 110 may recommend useful workout sequences, exercise videos, diet plans, etc., to help the user with their goals. In one embodiment, this tracking data may be used to predict the user's progress if the user continues on the same plan, such as a workout plan, or switch to another plan; or 7) taking and securing any unclothed photos of users using encryption or other methodologies, where the progress may be monitored better using depth measurements captured on previous photos and mapping those changes onto a generic human form.

In one embodiment, embodiments are not merely limited to humans and that they may be extended to plants, animals, etc., (such as domestic pets, wild animals, etc.) so that relevant individuals, such as botanists, zoologists, veterinarian, pet owners, etc., may track dimensions to determine progress or lack-thereof for a variety of purposes, such as plant growth, animal diet, etc. However, for the sake of brevity, clarity, and ease of understanding, persons/humans and their bodily dimensions are used for discussion throughout this document but that embodiments are not limited as such. Further, throughout the document, "user" may be referenced interchangeably with "person", "individual", "human", "him", "her", and/or the like.

In one embodiment, for example, a user having access to computing device 100 may choose to have own picture taken using a camera, such as depth-sensing camera 232, of capturing/sensing components 231. It is contemplated that embodiments are not limited to merely a user taking pictures of self and using own computing device, but that other persons and computing devices may also be used for these purposes, such as a physical trainer may use own computing device, such as computing device 270A, and/or a trainee's computing device, such as computing device 100, to take the trainee's pictures, and/or the like. However, for the sake of brevity, clarity, and ease of understanding, discussion throughout this document focuses on a user taking own pictures with own computing device 100 and then, as necessitated or desired, choosing to share the pictures with others (e.g., trainer, doctor, teacher, family, friends, etc.) using any number and type of computing devices, such as computing devices 270A-270C, over communication medium 260.

For example, the user's request to take a picture, such as pushing or clicking a relevant button at computing device, 100, may be detected by or received at detection/reception logic 201 and similarly, once a picture is taken by depth-sensing camera 232, the picture is also detected by detection/reception logic 201 along with any other information, such as depth information, relating to the picture is also received by detection/reception logic 201.

In one embodiment, the depth information along with the image (such as a full body image of the user's body, etc.) obtained from the picture is then forwarded on to analysis/model computation logic 203 where the depth information is used to compute measurement values relating to various body parts/areas of the user's body. For example, in analyzing the depth information in light of the image, analysis/model computation logic 203 may prepare dimension data identifying depth and/or disparity relating to bodily dimensions of various parts/areas of the body, such as chest size, waist size, stomach/belly size, overall height, etc. Similarly, in one embodiment, analysis/model computation logic 203 may be further used to generate a 3D model of the user's body based on the dimension data and/or using image, the depth information, etc.

Further, in one embodiment, the dimension data, the 3D model, any depth information, and/or the image obtained from the picture may then be sent over to be stored and maintained at one or more repositories, such as database(s) 265, in one or more formats, such as textual format, graphical format, mapping format, table format, etc. Additionally, the dimension data and/or the 3D model may be forwarded on to output components 233 so that any amount and type of dimension data and/or the 3D model may be displayed using a display device of output components 233. Similarly, this 3D model and/or the dimension data may be shared with others (e.g., parents, doctors, coaches, trainers, etc.) at their corresponding computing devices 270A-N over one or more networks of communication medium 260.

As previously discussed, in some cases, the user may choose to maintain the dimension data and/or the 3D model for tracking purposes to monitor progress, etc. In one embodiment, the dimension data and/or the 3D model may be received at tracking/comparing logic 205 to make a note of this development relating to the image and use it for tracking purposes, such as if the user chooses to have additional pictures taken in the future at various points in time, such as parents tracking their child's physical growth, a trainer tracking a trainee's results during a workout program, a doctor tracking a patient's progress relating to one or more body areas, a veterinarian tracking a pet's growth, and/or the like.

For example and in one embodiment, if the user chooses to take multiple pictures in order to track the progress, detection/reception logic 201 and analysis/model computation logic 203 may perform similar aforementioned processes with regard to each image as obtained from each of the multiple pictures, such as corresponding dimension data and 3D model may be computed for each picture, stored at database(s) 265, and provided on to tracking/comparing logic 205 for tracking purposes. Using multiple sets of dimension data and 3D models, tracking/comparing logic 205 may determine a pattern in changes incurred by various parts/areas of the user's body and further, based on those changes, tracking/comparing logic 205 may generate a tracking pattern encompassing dimension data/3D models relating to all images and/or depth information sets obtained from the multiple pictures and provide the tracking pattern in one or more formats, such as graphical format, mapping format, table format, etc., to be displayed using one or more display devices of output components 233 at computing device 100, input/output components 275 of computing device 270A, and/or the like.

As aforementioned, it is contemplated that a user may wish or need to achieve a target 3D model of the body or certain body dimensions relating to one or more body parts and accordingly, in one embodiment, the user may input a number of values using user interface 221 to generate a target 3D model as facilitated by target dimensions logic 207. For example, if the user wishes to reduce the waist size from 36 inches to 32 inches over a period of time, the user may input any relevant information (e.g., current waist size, target waist size, height, time period over which to achieve the target, eating habits, exercise or workout plan, etc.), where this relevant information may be used by target dimensions logic 207 to generate a target 3D model of the user's body, wherein this 3D model reflects the user goal with regard to the waist size.

In some embodiments, the user may choose to generate multiple target 3D models as facilitated by target dimensions logic 207, such as when the user may want the various target 3D models to serve as a small milestone until reaching the final target 3D model. Similarly, the user may choose to generate multiple target 3D models, as facilitated by target dimensions logic 207, based on the difficulty associated with each target 3D model, such as conservative target, moderate target, aggressive target, etc. Further, in one embodiment, the user may choose to alter one or more target 3D models, via user interface 215 and as facilitated by target dimensions logic 207, for any number and type of reasons, such as change of mind, circumstances, workout plan, doctor/trainer recommendation, etc.

In one embodiment, a new target 3D model (and any additional target 3D models) may be communicated to tracking/comparing logic 205 so that the user's goal (e.g., 32-inch wait, etc.) is known as tracking/comparing logic 205 monitors and/or tracks the user's progress (such as with regard to the waist size).

Further, in one embodiment, various images collected from the multiple pictures taken by depth-sensing camera(s) 232 may be put together to generate a single image that is reflective of any changes in the users' body dimensions. For example, if a picture was taken every week over a 10-week period, the user may trigger the stitching or merging feature by accessing user interface 221 such that upon receiving a stitching/merging request, stitching/merging logic 209 may be triggered to merge together the 10 pictures taken over the 10-week period of time to generate a single image that is easier for the user to view for analyzing the user's progress over the 10-week period. It is contemplated that not all images, such as all 10 images, are required to be merged or stitched into a single image. For example and in one embodiment, the user may select a smaller number of images, such as 5 images, 7 images, etc., to stitched into a single image. Further, in one embodiment, the selected set of images do not need to be in a sequence, such as the first 5 images or the last 7 images, etc., but that the user may, using user interface 221, select any number of images in any sequence, such as the 5 selected images may include images 1, 3, 5, 8, and 10, and/or the like.

In one embodiment, as with multiple images, stitching/merging logic 209 may be used to merge any number of 3D models into a single 3D model, such as merging multiple 3D models corresponding to multiple images into a single 3D model. Further, as with multiple images, not all available 3D models are to be selected for merging and further, the selected 3D models do not need to be in any particular sequence. In some embodiments, these 3D models include automatically generated 3D models corresponding to images and/or user-initiated target 3D models.

In one embodiment, recommendation/prediction logic 211 may then be triggered to generate and provide predictions and/or recommendations based on one or more 3D models and/or one or more target 3D models. For example and in one embodiment, stitching/merging logic 208 may be used to compare a 3D model with a target 3D model to determine whether the user is on the right track with regard to his/her goals, such as does the 3D model, when compared to the target 3D model, suggest that user will be able to reduce the size of the waist to 32 inches in the remaining 10 days, etc. For example, if results of the comparison provide that the user is not likely to reach the goal as set forth in the target 3D model, recommendation/prediction logic 211 may generate and recommend one or more alternative plans to help achieve the goal in the remaining time, where the one or more alternative plans may include a different workout routing, a modified diet plan, and/or the like.

Similarly, in one embodiment, recommendation/prediction logic 211 offers predictability features where, for example, using the aforementioned comparison results and/or other relevant information, recommendation/prediction logic 211 may also be capable of predicting the user's progress, such as whether the progress will reach the goal, how close the user will get to the goal, how many more or less days the user will needs to achieve the goal, and/or the like. In one embodiment, any recommendations and/or predictions may be communicated on to the user and/or other relevant individuals (e.g., trainer, doctors, etc.) so that the user may have sufficient information to decided whether there is a need to modify anything, such as the user's goal, the workout plan, eating habits, overall or specific expectations, and/or the like. These recommendations and/or predictions may be displayed to the user and/or other relevant individuals using one or more display devices in communication with their corresponding computing devices 100, 270A-N, wherein, for example, various users may choose to take certain measures to keep up with the predictions by maintaining or modifying their ways, as desired or necessitated.

It is contemplated that in some circumstances, certain pictures of users may be private in nature, such as taken without some or all clothes for better measurement and viewing of body dimensions for medical, health, psychological, and other similar reasons, etc. Further, in some cases, users may choose to take such private pictures without any particular need for them except to be able to take proper look at certain body parts and/or areas to better monitor changes in overall body dimensions and specific dimensions of certain body parts/areas, and/or the like, over a period of time. Given the private and compromising nature of certain pictures, in one embodiment, privacy logic 213 may be triggered and used to secure the user's privacy by encrypting the images or certain parts of the images (e.g., private body parts) using one or more encrypting techniques. Further, for example, privacy logic 213 may be used to monitor and map any changes in the body dimensions to a more generic human form for the users' benefit without disclosing any of the personal parts from the images and thus keeping the images secure and private.

As previously disclosed, user interface logic 215 may be used to offer user interface 221 that may be accessed by the user having access to computing device 100 to use smart dimensions mechanism 110 and one or more other components, such as capturing/sensing components 231, such as depth-sensing camera 232, and output components, such as a display device, etc.

Communication/compatibility logic 217 may be used to facilitate dynamic communication and compatibility between computing devices 100, 270A-N, database(s) 265, communication medium 260, etc., and any number and type of other computing devices (such as wearable computing devices, mobile computing devices, desktop computers, server computing devices, etc.), processing devices (e.g., central processing unit (CPU), graphics processing unit (GPU), etc.), capturing/sensing components (e.g., non-visual data sensors/detectors, such as audio sensors, olfactory sensors, haptic sensors, signal sensors, vibration sensors, chemicals detectors, radio wave detectors, force sensors, weather/temperature sensors, body/biometric sensors, scanners, etc., and visual data sensors/detectors, such as cameras, etc.), user/context-awareness components and/or identification/verification sensors/devices (such as biometric sensors/detectors, scanners, etc.), memory or storage devices, data sources, and/or database(s) (such as data storage devices, hard drives, solid-state drives, hard disks, memory cards or devices, memory circuits, etc.), network(s) (e.g., Cloud network, the Internet, Internet of Things, intranet, cellular network, proximity networks, such as Bluetooth, Bluetooth low energy (BLE), Bluetooth Smart, Wi-Fi proximity, Radio Frequency Identification (RFID), Near Field Communication (NFC), Body Area Network (BAN), etc.), wireless or wired communications and relevant protocols (e.g., Wi-Fi®, WiMAX, Ethernet, etc.), connectivity and location management techniques, software applications/websites, (e.g., social and/or business networking websites, business applications, games and other entertainment applications, etc.), programming languages, etc., while ensuring compatibility with changing technologies, parameters, protocols, standards, etc.

Throughout this document, terms like "logic", "component", "module", "framework", "engine", "tool", and the like, may be referenced interchangeably and include, by way of example, software, hardware, and/or any combination of software and hardware, such as firmware. In one example, "logic" may refer to or include a software component that is capable of working with one or more of an operating system, a graphics driver, etc., of a computing device, such as computing device 100. In another example, "logic" may refer to or include a hardware component that is capable of being physically installed along with or as part of one or more system hardware elements, such as an application processor, a graphics processor, etc., of a computing device, such as computing device 100. In yet another embodiment, "logic" may refer to or include a firmware component that is capable of being part of system firmware, such as firmware of an application processor or a graphics processor, etc., of a computing device, such as computing device 100.

Further, any use of a particular brand, word, term, phrase, name, and/or acronym, such as "body", "body dimension", "body part", "body area", "picture", "image", "depth-sensing camera", "monitoring", "stitching", "privacy", "user", "user profile", "user preference", "user", "sender", "receiver", "personal device", "smart device", "mobile computer", "wearable device", etc., should not be read to limit embodiments to software or devices that carry that label in products or in literature external to this document.

It is contemplated that any number and type of components may be added to and/or removed from smart dimensions mechanism 110 to facilitate various embodiments including adding, removing, and/or enhancing certain features. For brevity, clarity, and ease of understanding of smart dimensions mechanism 110, many of the standard and/or known components, such as those of a computing device, are not shown or discussed here. It is contemplated that embodiments, as described herein, are not limited to any particular technology, topology, system, architecture, and/or standard and are dynamic enough to adopt and adapt to any future changes.

Figure 3:
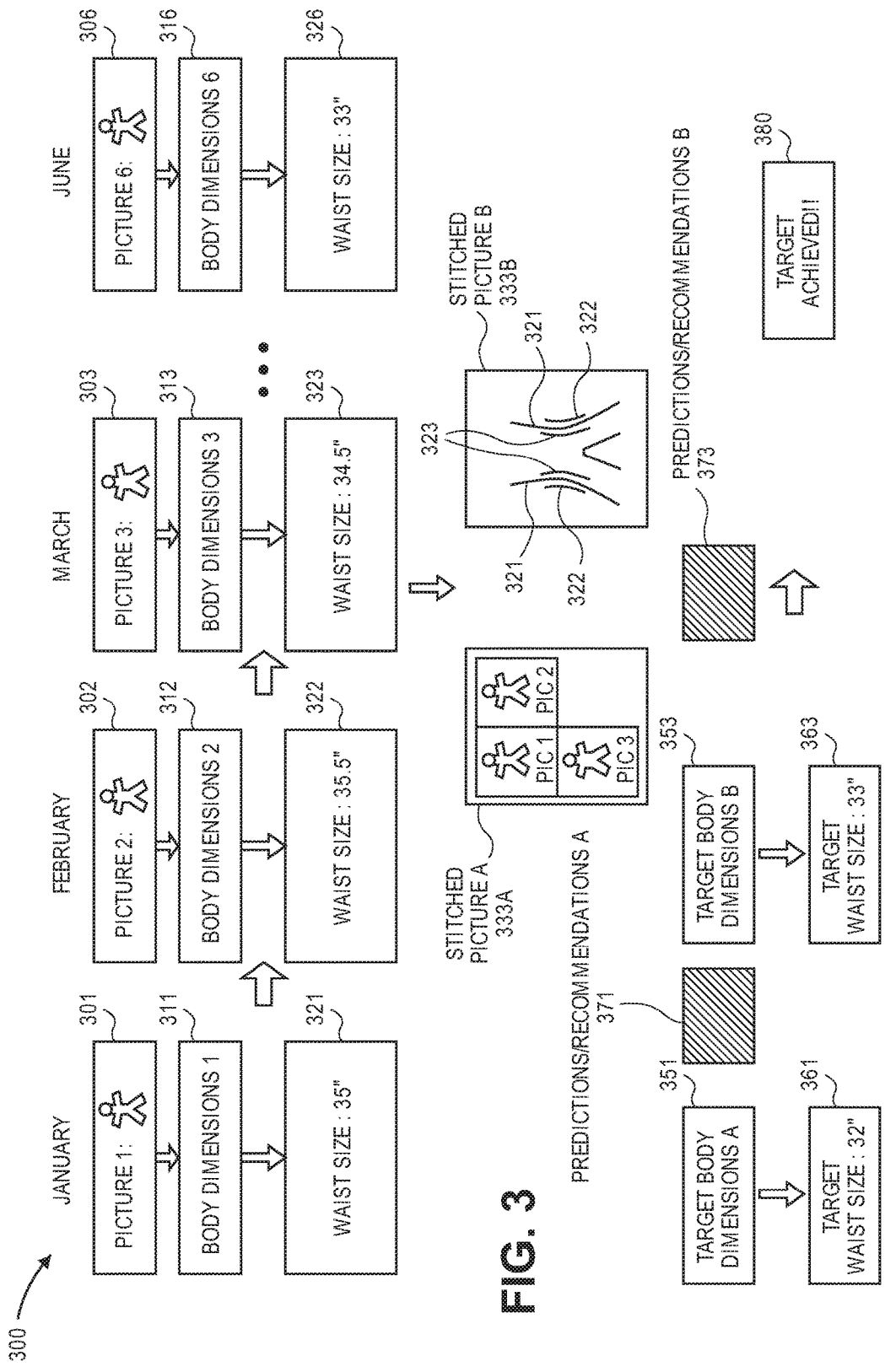
FIG. 3 illustrates a transaction sequence for smart monitoring of body dimensions according to one embodiment.

FIG. 3 illustrates a transaction sequence 300 for smart monitoring of body dimensions according to one embodiment. Transaction sequence 300 may be performed by processing logic that may comprise hardware (e.g., circuitry, dedicated logic, programmable logic, etc.), software (such as instructions run on a processing device), or a combination thereof. In one embodiment, transaction sequence 300 may be performed by smart dimensions mechanism 110 of FIGS. 1-2. The processes of transaction sequence 300 are illustrated in linear sequences for brevity and clarity in presentation; however, it is contemplated that any number of them can be performed in parallel, asynchronously, or in different orders. For brevity, many of the details discussed with reference to the previous figures may not be discussed or repeated hereafter.

For example, a user decides on a new year's resolution to lose his waist from 35 inches to 32 inches. Accordingly, in January, using a user interface, such as user interface 221, 273, etc., in one embodiment, the user sets up target body dimensions A 351 of his own body that includes target waist 361 of 32 inches. With that in mind, using a depth-sensing camera, such as depth-sensing camera(s) 234, 276, the user takes or have someone else take a picture, such as picture 1 301, that shows the user entire body and/or the relevant parts of the body, such as the waist. In one embodiment, using the image, such as image 1, of picture 1 301 and depth information as obtained from the depth-sensing camera, body dimensions 1 311 are extracted or computed, where the current waist size, such as waist 321, is shown to be 35 inches at the time picture 1 301 was taken in January.

As described throughout this document, in one embodiment, the user may be offered predictions and/or recommendations in relations to the user's aspirations as reflected in target body dimensions A 351 and the overall progress from picture to picture. For example, in one embodiment, in February, picture 2 302 is taken and body dimensions 2 312 are computed, where body dimensions 2 312 show current waist size 2 322 to be 35.5 inches. With the increase in waist size, recommendation/prediction logic 211 of smart dimensions mechanism 110 of FIG. 2 may offer one or more predictions and/or recommendations, such as predictions/recommendations A 371, to the user.

For example, a prediction in predictions/recommendations A 371 may indicate the probability (such as 35% chance by June) of the user reaching his target waist 361 of 32 inches, where a recommendation may include (without limitations) a new target waist size, a new or modified workout plan, a new or modified diet plan, a new or modified sleep schedule, a new trainee, a new or modified time period, such September instead of June or June 30 as opposed to June 1, and/or the like. For example, in this case, the user chooses to modify the target waist size to be a more realistic one, such as, based on predictions/recommendations A 371, target waist 361 of 32 inches is changed to target waist of 33 inches by entering a new set of target body dimensions, such as target body dimensions B 353 replacing target body dimensions A 351. It is contemplated that user may choose to follow one or more other recommendations as well, such as a modified workout plan, a new diet plan, etc., along with altering the waist size from 361 (32 inches) 361 to 363 (33 inches).

In one embodiment, transaction sequence 300 continues to another month, such as March, when picture 3 303 is taken and new body dimensions 3 313 are obtained from it, where body dimensions 3 313 indicates a new waist size, such as waist 323, to be 34.5 inches. This new size indicates progress over the original size of waist 321 of 35 inches.

At any point after taking the first two pictures 301, 301, the user may choose to request a stitched picture as facilitated by stitching/merging logic 209 of smart dimensions mechanism 110 of FIG. 2. For example, after having taken the first three pictures, such as pictures 1 301, 2 302, and 3 303 in January, February, and March, respectively, the user may request one or more stitched pictures, such as, in one embodiment, stitched picture A 333A that lays out the existing pictures 1 301, 2 302, 3 303, side-by-side, such that each picture (e.g., picture 3 303) may be easily visually compared by the user with any one or more of the other pictures (e.g., picture 1 301, picture 2 302) in stitched picture A 333A. Similarly, in another embodiment, a different form of stitched picture, such as stitched picture B 333B, may be requested and generated which provides an overlapping set of pictures 1 301, 2 302, 3 303 (as opposed to side-by-side placement of stitched picture A 333A) such that the user may easily visualize any differences in his body dimensions relating to the entire body and/or any particular areas of the body, such as changes in waist sizes 321, 322, 323, etc.

Further, in one embodiment, at any point after generating and presenting predictions/recommendations A 371, one or more other sets of predictions and/or recommendations, such as predictions/recommendations B 373, may be generated and presented to the user via a display devices to assist the user in predictions, recommendations, etc., as discussed above.

It is contemplated that the user may continue to have pictures taken as often as desired or necessary, such as each day, week, month, etc. In this example, however, let us suppose new pictures are taken in April and May and finally, a last picture 6 306 is taken in June, a last set of body dimensions 6 316 is computed, where this last set of body dimensions 6 316 indicate the user's current waist size 326 to be 33 inches which is the same as the user's target waist 363 of 33 inches. Since, in this example, the user is shown to have achieved his goal with regard to the waist size, as set forth in target body dimensions B 353 and target waist 363, a notification message may be communicated to the user, such as using a user interface and via a display device, where such notification message may include a note, such as "Target Achieved!", "Congratulations!", "Goal!!!", and/or the like.

Figure 4A:
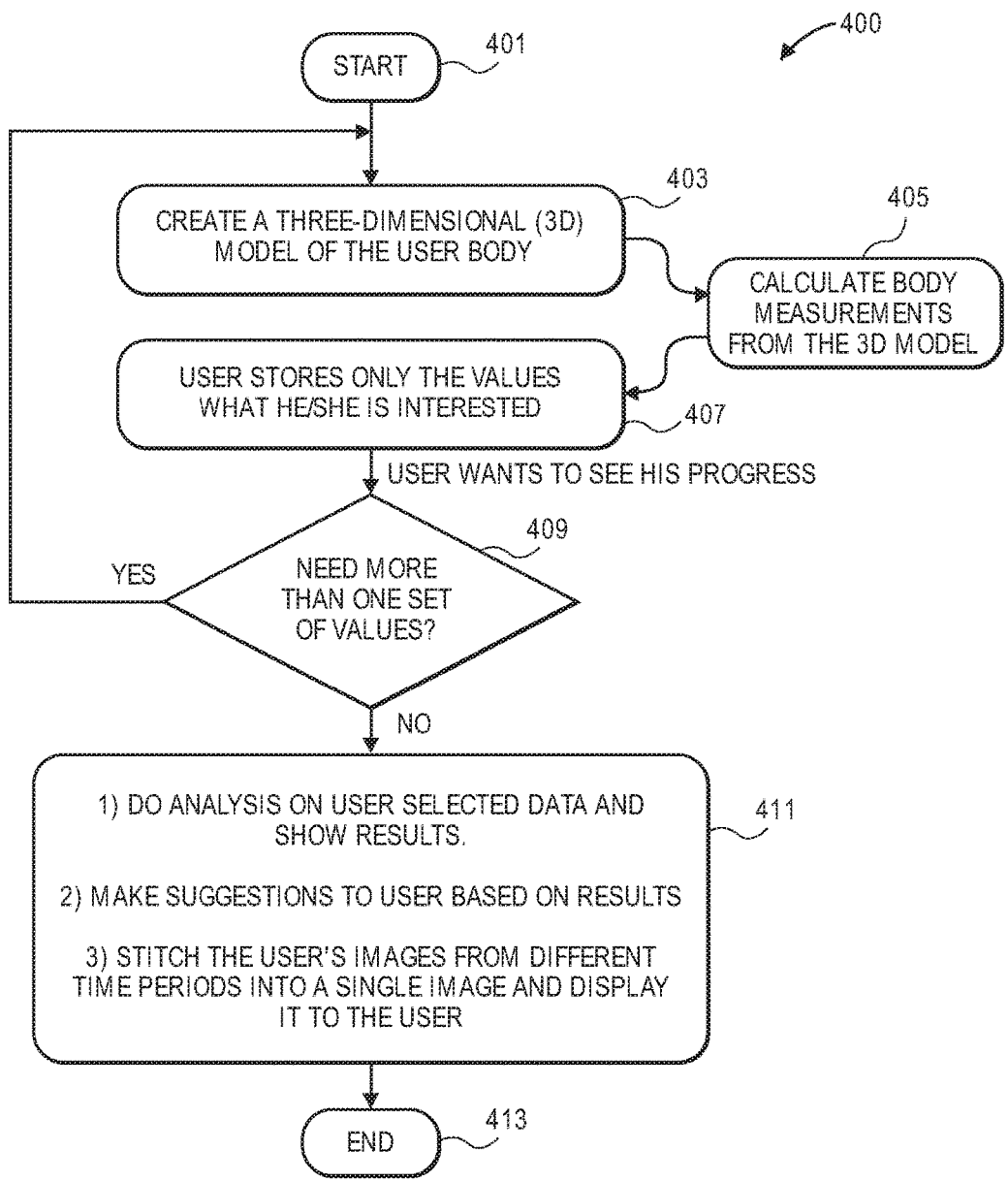
FIG. 4A illustrates a method for smart monitoring of body dimensions according to one embodiment.

FIG. 4A illustrates a method 400 for smart monitoring of body dimensions according to one embodiment. Method 400 may be performed by processing logic that may comprise hardware (e.g., circuitry, dedicated logic, programmable logic, etc.), software (such as instructions run on a processing device), or a combination thereof. In one embodiment, method 400 may be performed by smart dimensions mechanism 110 of FIGS. 1-3. The processes of method 400 are illustrated in linear sequences for brevity and clarity in presentation; however, it is contemplated that any number of them can be performed in parallel, asynchronously, or in different orders. For brevity, many of the details discussed with reference to the previous figures may not be discussed or repeated hereafter.

Method 400 starts at block 401 and the process begins at block 403 with creation of a 3D model of a user's body, where the 3D model is generated based on an image and its corresponding depth information obtained from a picture taken by a depth-sensing camera (e.g., Intel® RealSense™ camera) of a computing device. At block 405, in one embodiment, various values, such as measurements, dimensions, etc., of the overall body and/or one or more parts/areas of the body may be obtained from or computed based on the 3D model. At block 407, all or some of the values may be stored, such as at a database, as, for example, chosen by the user or others as necessitated or desired.

In one embodiment, at block 409, a determination is made at to whether additional sets of values are needed. If not, such as if, for example, the stored values extracted from the image obtained from the aforementioned single picture are sufficient for the user, method 400 may then continue with further analysis of the stored values at block 411. If yes, such as if, for example, additional values are needed for when the user (or the user's trainer, doctor, etc.) wishes to monitor the body dimensions of the user over a period of time, etc., more pictures of the user's body and/or certain body parts may be needed and accordingly, method 400 may continue with taking additional pictures at various points in time and generating their corresponding 3D models at block 403.

Referring back to block 411, the analysis may include evaluating the selected values to extract current body dimensions, comparing values of one image with values of other images to determine any changes/progress in body dimensions, predicting the user's progress based on any changes in the user's body dimensions, merging or stitching the user's multiple images into fewer images or a single image, and/or the like, and forward the relevant data to one or more display devices in communication with one or more computing devices for viewing of the user and any other relevant users. Method 400 ends at block 413.

Figure 4B:
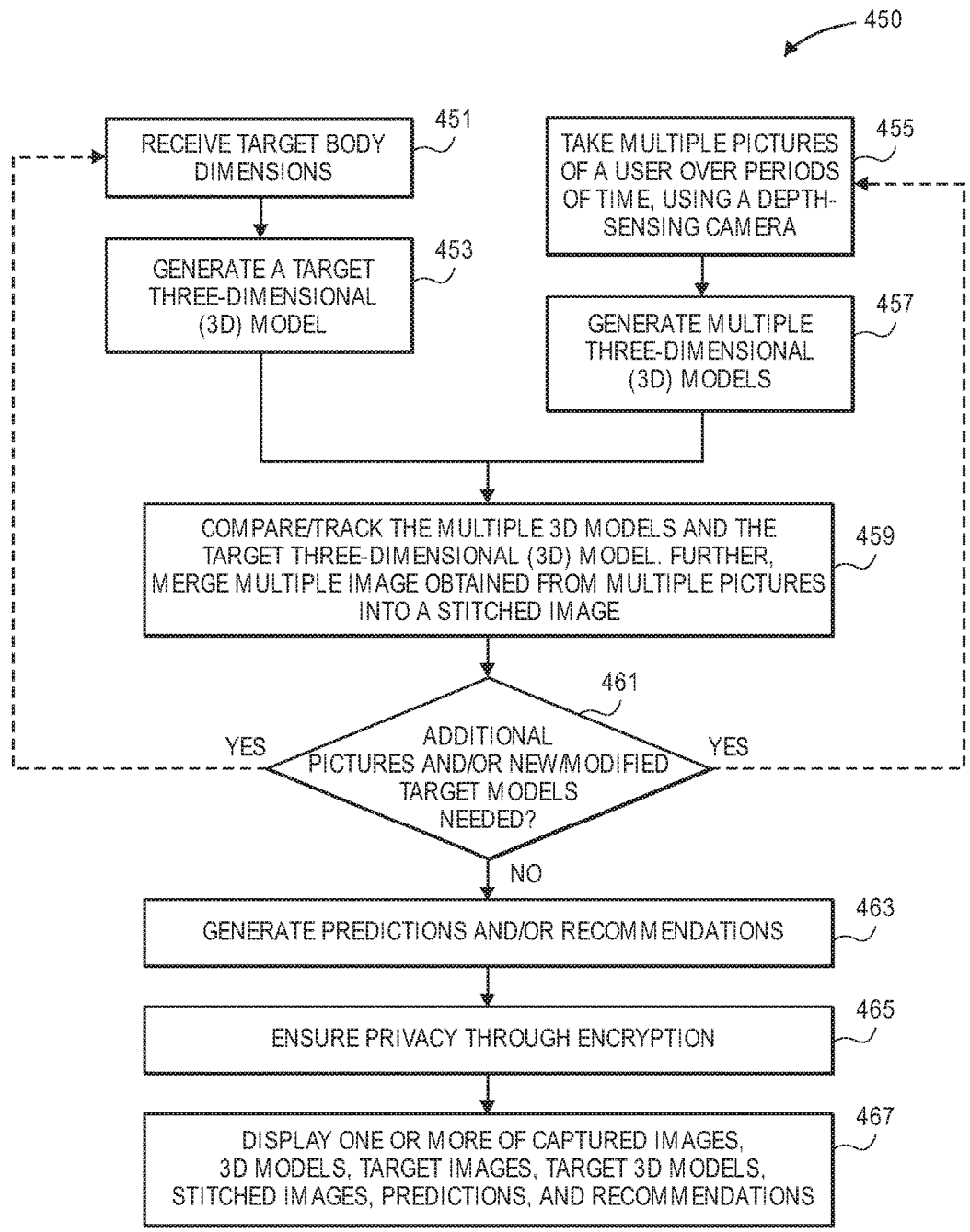
FIG. 4B illustrates a method for smart monitoring of body dimensions according to one embodiment.

FIG. 4B illustrates a method 450 for smart monitoring of body dimensions according to one embodiment. Method 450 may be performed by processing logic that may comprise hardware (e.g., circuitry, dedicated logic, programmable logic, etc.), software (such as instructions run on a processing device), or a combination thereof. In one embodiment, method 450 may be performed by smart dimensions mechanism 110 of FIGS. 1-4A. The processes of method 450 are illustrated in linear sequences for brevity and clarity in presentation; however, it is contemplated that any number of them can be performed in parallel, asynchronously, or in different orders. For brevity, many of the details discussed with reference to the previous figures may not be discussed or repeated hereafter.

Method 450 may begin at block 451 with receiving target body dimensions from a user via a user interface at a computing device, where the target body dimensions reflect a target image of the user's body, such as a target body or body parts aspired by the user. In one embodiment, the target 3D model may be generated based on a past picture of the user, personal data provided by the user (e.g., desired waist size, overall weight, expected chest size, etc.), a picture or data of another person (e.g., celebrity picture, friend's picture, sibling's picture, etc.), and/or the like. At block 453, a target 3D model is generated based on the target body dimensions along with any other relevant data (e.g., user preferences, user criteria, etc.) provided by the user.

It is contemplated that embodiments do not require for the user to have a target 3D model, but embodiments provide for a novel technique to allow the user to pursue a goal based on a target 3D model. Further, embodiments are not limited to a single target 3D model and that the user may choose to enter personal data to generate additional target 3D models. For example, multiple target models may correspond to incremental progress points (e.g., model 1 at week 1, model 2 at week 2 and so forth), while, in some cases, a new or modified target 3D model may be needed each time the user changes his/her mind and modifies his/her goal and/or if the relevant circumstances are altered (e.g., not as much time left to reach a previous target), etc. It is further contemplated that multiple sets of target body dimensions may be entered simultaneously (such as when corresponding to incremental progress points, etc.) or over separately over a period of time (such as every week, every month, etc., or each time the user's goals have changed or the relevant circumstances have altered, etc.).

At block 455, in one embodiment, method 450 continues with taking of the user's multiple pictures using a depth-sensing camera (e.g., Intel® RealSense™ camera) at the computing device (e.g., smartphone, table computer, wearable device, laptop computer, etc.). It is contemplated that embodiments are not limited to merely still pictures and that pictures may include videos and other forms of photos, etc. It is further contemplated that the pictures may be taken using any number and type of computing devices accessible to the user and/or other users, such as the user's trainer, doctor, parents, teachers, friends, family, etc. At block 457, multiple 3D models are generated based on the multiple pictures based on images, sets of depth information, etc., obtained from the corresponding pictures.

At block 459, in one embodiment, two or more of the multiple 3D models may be compared with each other to detect any changes in body dimensions (e.g., waist size, etc.) of the user to determine whether any progress, or lack-thereof, has been made over a period of time. Further, in one embodiment, one or more of the multiple 3D models may be compared with the target 3D model to determine the user's progress in terms of the body dimensions against the target 3D models indicative of the user's goal with regard to his/her body dimensions. Further, at block 455, in one embodiment, multiple images obtained from the corresponding multiple pictures may be stitched or merged together into one or more image so that a better overall image may be offered to the user to better understand his/her body dimensions and any progress or lack-thereof with that regard.

As previously discussed, in one embodiment, the user may choose to generate additional target 3D models, modify the existing target 3D model, take additional pictures, and/or the like, and such determination is made at block 461. If yes, method 450 may continue with taking of one or more additional pictures at block 455, and/or receiving of new target body dimensions at block 451, where the new target body dimensions may be used to generate and add a new target 3D model or modify the existing target 3D model. If not, method 450 continues at block 463 with generating of predictions and/or recommendations based on comparison results obtained from one or more processes of block 459.

It is contemplated that certain pictures may reveal one or more parts of the user's body or other surrounding or relevant information (e.g., name, address, etc.) that may be regarded as personal or private and accordingly, in one embodiment, at block 465, such images, certain portions of images, other personal information, etc., may be encrypted using one or more encryption techniques to secure and preserve the user's privacy. At block 467, one or more of captured images and their 3D models, target images and their target 3D models, stitched images, predictions, and/or recommendations are displayed at one or more display devices of one or more computing devices accessible to the user and one or more other relevant users.

Figure 5:
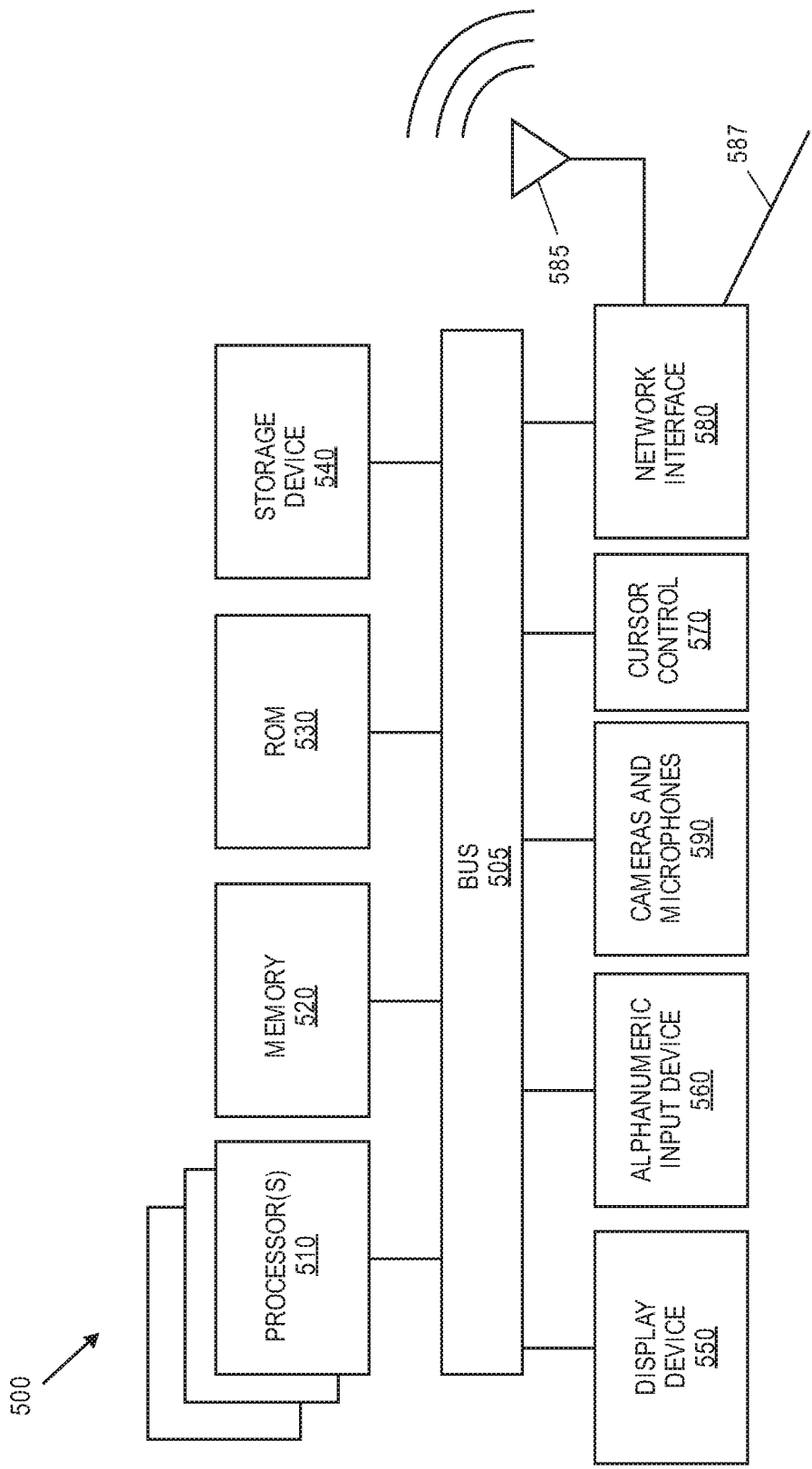
FIG. 5 illustrates computer environment suitable for implementing embodiments of the present disclosure according to one embodiment.

FIG. 5 illustrates an embodiment of a computing system 500 capable of supporting the operations discussed above. Computing system 500 represents a range of computing and electronic devices (wired or wireless) including, for example, desktop computing systems, laptop computing systems, cellular telephones, personal digital assistants (PDAs) including cellular-enabled PDAs, set top boxes, smartphones, tablets, wearable devices, etc. Alternate computing systems may include more, fewer and/or different components. Computing device 500 may be the same as or similar to or include computing devices 100 described in reference to FIG. 1.

Computing system 500 includes bus 505 (or, for example, a link, an interconnect, or another type of communication device or interface to communicate information) and processor 510 coupled to bus 505 that may process information. While computing system 500 is illustrated with a single processor, it may include multiple processors and/or co-processors, such as one or more of central processors, image signal processors, graphics processors, and vision processors, etc. Computing system 500 may further include random access memory (RAM) or other dynamic storage device 520 (referred to as main memory), coupled to bus 505 and may store information and instructions that may be executed by processor 510. Main memory 520 may also be used to store temporary variables or other intermediate information during execution of instructions by processor 510.

Computing system 500 may also include read only memory (ROM) and/or other storage device 530 coupled to bus 505 that may store static information and instructions for processor 510. Date storage device 540 may be coupled to bus 505 to store information and instructions. Date storage device 540, such as magnetic disk or optical disc and corresponding drive may be coupled to computing system 500.

Computing system 500 may also be coupled via bus 505 to display device 550, such as a cathode ray tube (CRT), liquid crystal display (LCD) or Organic Light Emitting Diode (OLED) array, to display information to a user. User input device 560, including alphanumeric and other keys, may be coupled to bus 505 to communicate information and command selections to processor 510. Another type of user input device 560 is cursor control 570, such as a mouse, a trackball, a touchscreen, a touchpad, or cursor direction keys to communicate direction information and command selections to processor 510 and to control cursor movement on display 550. Camera and microphone arrays 590 of computer system 500 may be coupled to bus 505 to observe gestures, record audio and video and to receive and transmit visual and audio commands.

Computing system 500 may further include network interface(s) 580 to provide access to a network, such as a local area network (LAN), a wide area network (WAN), a metropolitan area network (MAN), a personal area network (PAN), Bluetooth, a cloud network, a mobile network (e.g., 3$^{rd}$ Generation (3G), etc.), an intranet, the Internet, etc. Network interface(s) 580 may include, for example, a wireless network interface having antenna 585, which may represent one or more antenna(e). Network interface(s) 580 may also include, for example, a wired network interface to communicate with remote devices via network cable 587, which may be, for example, an Ethernet cable, a coaxial cable, a fiber optic cable, a serial cable, or a parallel cable.

Network interface(s) 580 may provide access to a LAN, for example, by conforming to IEEE 802.11b and/or IEEE 802.11g standards, and/or the wireless network interface may provide access to a personal area network, for example, by conforming to Bluetooth standards. Other wireless network interfaces and/or protocols, including previous and subsequent versions of the standards, may also be supported.

In addition to, or instead of, communication via the wireless LAN standards, network interface(s) 580 may provide wireless communication using, for example, Time Division, Multiple Access (TDMA) protocols, Global Systems for Mobile Communications (GSM) protocols, Code Division, Multiple Access (CDMA) protocols, and/or any other type of wireless communications protocols.

Network interface(s) 580 may include one or more communication interfaces, such as a modem, a network interface card, or other well-known interface devices, such as those used for coupling to the Ethernet, token ring, or other types of physical wired or wireless attachments for purposes of providing a communication link to support a LAN or a WAN, for example. In this manner, the computer system may also be coupled to a number of peripheral devices, clients, control surfaces, consoles, or servers via a conventional network infrastructure, including an Intranet or the Internet, for example.

It is to be appreciated that a lesser or more equipped system than the example described above may be preferred for certain implementations. Therefore, the configuration of computing system 500 may vary from implementation to implementation depending upon numerous factors, such as price constraints, performance requirements, technological improvements, or other circumstances. Examples of the electronic device or computer system 500 may include without limitation a mobile device, a personal digital assistant, a mobile computing device, a smartphone, a cellular telephone, a handset, a one-way pager, a two-way pager, a messaging device, a computer, a personal computer (PC), a desktop computer, a laptop computer, a notebook computer, a handheld computer, a tablet computer, a server, a server array or server farm, a web server, a network server, an Internet server, a work station, a mini-computer, a main frame computer, a supercomputer, a network appliance, a web appliance, a distributed computing system, multiprocessor systems, processor-based systems, consumer electronics, programmable consumer electronics, television, digital television, set top box, wireless access point, base station, subscriber station, mobile subscriber center, radio network controller, router, hub, gateway, bridge, switch, machine, or combinations thereof.

Embodiments may be implemented as any or a combination of: one or more microchips or integrated circuits interconnected using a parentboard, hardwired logic, software stored by a memory device and executed by a microprocessor, firmware, an application specific integrated circuit (ASIC), and/or a field programmable gate array (FPGA). The term "logic" may include, by way of example, software or hardware and/or combinations of software and hardware.

Embodiments may be provided, for example, as a computer program product which may include one or more transitory or non-transitory machine-readable storage media having stored thereon machine-executable instructions that, when executed by one or more machines such as a computer, network of computers, or other electronic devices, may result in the one or more machines carrying out operations in accordance with embodiments described herein. A machine-readable medium may include, but is not limited to, floppy diskettes, optical disks, CD-ROMs (Compact Disc-Read Only Memories), and magneto-optical disks, ROMs, RAMs, EPROMs (Erasable Programmable Read Only Memories), EEPROMs (Electrically Erasable Programmable Read Only Memories), magnetic or optical cards, flash memory, or other type of media/machine-readable medium suitable for storing machine-executable instructions.

Moreover, embodiments may be downloaded as a computer program product, wherein the program may be transferred from a remote computer (e.g., a server) to a requesting computer (e.g., a client) by way of one or more data signals embodied in and/or modulated by a carrier wave or other propagation medium via a communication link (e.g., a modem and/or network connection).

References to "one embodiment", "an embodiment", "example embodiment", "various embodiments", etc., indicate that the embodiment(s) so described may include particular features, structures, or characteristics, but not every embodiment necessarily includes the particular features, structures, or characteristics. Further, some embodiments may have some, all, or none of the features described for other embodiments.

In the following description and claims, the term "coupled" along with its derivatives, may be used. "Coupled" is used to indicate that two or more elements co-operate or interact with each other, but they may or may not have intervening physical or electrical components between them.

As used in the claims, unless otherwise specified the use of the ordinal adjectives "first", "second", "third", etc., to describe a common element, merely indicate that different instances of like elements are being referred to, and are not intended to imply that the elements so described must be in a given sequence, either temporally, spatially, in ranking, or in any other manner.

Figure 6:
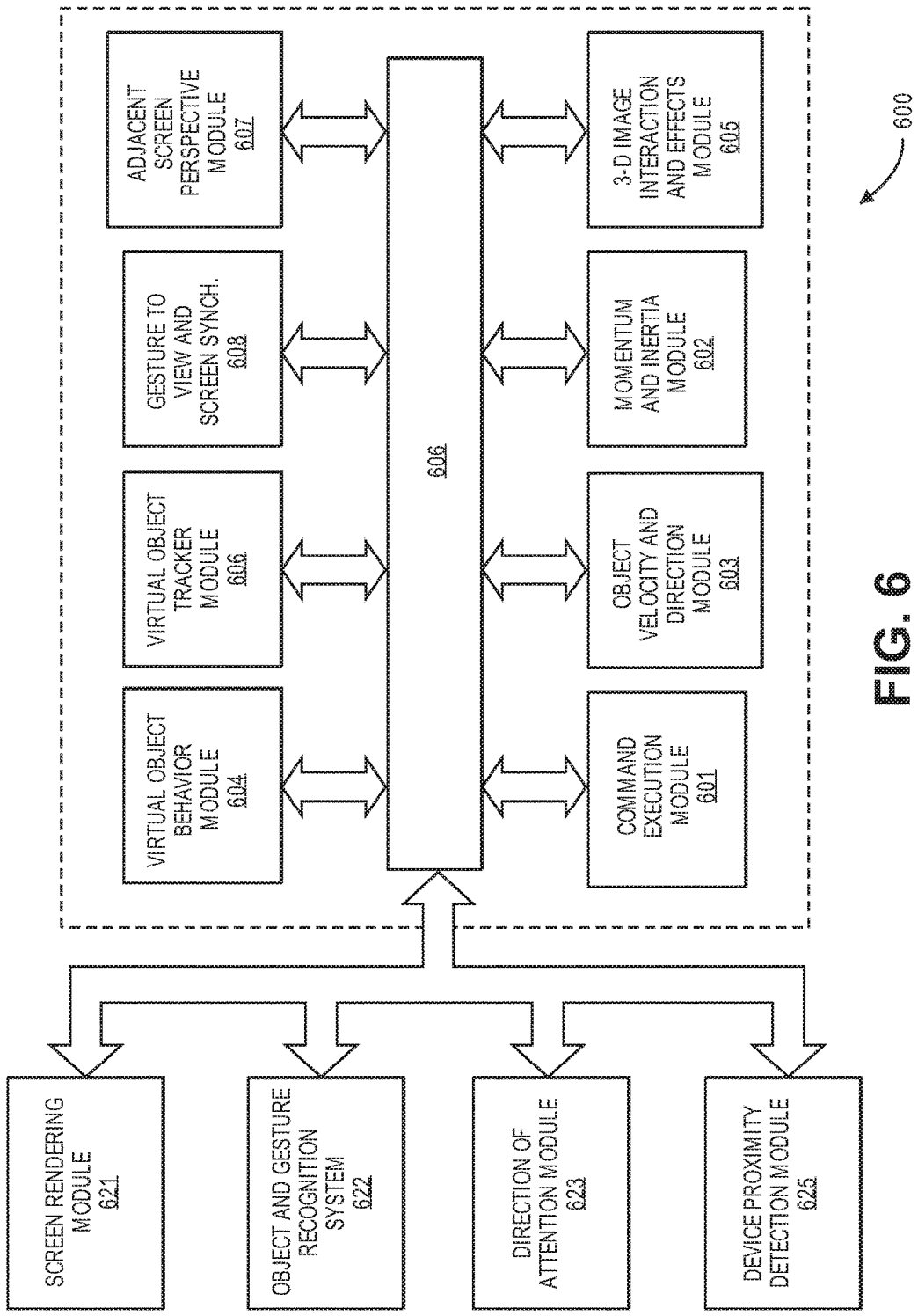
FIG. 6 illustrates a method for facilitating dynamic targeting of users and communicating of message according to one embodiment.

FIG. 6 illustrates an embodiment of a computing environment 600 capable of supporting the operations discussed above. The modules and systems can be implemented in a variety of different hardware architectures and form factors including that shown in FIG. 4.

The Command Execution Module 601 includes a central processing unit to cache and execute commands and to distribute tasks among the other modules and systems shown. It may include an instruction stack, a cache memory to store intermediate and final results, and mass memory to store applications and operating systems. The Command Execution Module may also serve as a central coordination and task allocation unit for the system.

The Screen Rendering Module 621 draws objects on the one or more multiple screens for the user to see. It can be adapted to receive the data from the Virtual Object Behavior Module 604, described below, and to render the virtual object and any other objects and forces on the appropriate screen or screens. Thus, the data from the Virtual Object Behavior Module would determine the position and dynamics of the virtual object and associated gestures, forces and objects, for example, and the Screen Rendering Module would depict the virtual object and associated objects and environment on a screen, accordingly. The Screen Rendering Module could further be adapted to receive data from the Adjacent Screen Perspective Module 607, described below, to either depict a target landing area for the virtual object if the virtual object could be moved to the display of the device with which the Adjacent Screen Perspective Module is associated. Thus, for example, if the virtual object is being moved from a main screen to an auxiliary screen, the Adjacent Screen Perspective Module 2 could send data to the Screen Rendering Module to suggest, for example in shadow form, one or more target landing areas for the virtual object on that track to a user's hand movements or eye movements.

The Object and Gesture Recognition System 622 may be adapted to recognize and track hand and arm gestures of a user. Such a module may be used to recognize hands, fingers, finger gestures, hand movements and a location of hands relative to displays. For example, the Object and Gesture Recognition Module could for example determine that a user made a body part gesture to drop or throw a virtual object onto one or the other of the multiple screens, or that the user made a body part gesture to move the virtual object to a bezel of one or the other of the multiple screens. The Object and Gesture Recognition System may be coupled to a camera or camera array, a microphone or microphone array, a touch screen or touch surface, or a pointing device, or some combination of these items, to detect gestures and commands from the user.

The touch screen or touch surface of the Object and Gesture Recognition System may include a touch screen sensor. Data from the sensor may be fed to hardware, software, firmware or a combination of the same to map the touch gesture of a user's hand on the screen or surface to a corresponding dynamic behavior of a virtual object. The sensor date may be used to momentum and inertia factors to allow a variety of momentum behavior for a virtual object based on input from the user's hand, such as a swipe rate of a user's finger relative to the screen. Pinching gestures may be interpreted as a command to lift a virtual object from the display screen, or to begin generating a virtual binding associated with the virtual object or to zoom in or out on a display. Similar commands may be generated by the Object and Gesture Recognition System using one or more cameras without benefit of a touch surface.

The Direction of Attention Module 623 may be equipped with cameras or other sensors to track the position or orientation of a user's face or hands. When a gesture or voice command is issued, the system can determine the appropriate screen for the gesture. In one example, a camera is mounted near each display to detect whether the user is facing that display. If so, then the direction of attention module information is provided to the Object and Gesture Recognition Module 622 to ensure that the gestures or commands are associated with the appropriate library for the active display. Similarly, if the user is looking away from all of the screens, then commands can be ignored.

The Device Proximity Detection Module 625 can use proximity sensors, compasses, GPS (global positioning system) receivers, personal area network radios, and other types of sensors, together with triangulation and other techniques to determine the proximity of other devices. Once a nearby device is detected, it can be registered to the system and its type can be determined as an input device or a display device or both. For an input device, received data may then be applied to the Object Gesture and Recognition System 622. For a display device, it may be considered by the Adjacent Screen Perspective Module 607.

The Virtual Object Behavior Module 604 is adapted to receive input from the Object Velocity and Direction Module, and to apply such input to a virtual object being shown in the display. Thus, for example, the Object and Gesture Recognition System would interpret a user gesture and by mapping the captured movements of a user's hand to recognized movements, the Virtual Object Tracker Module would associate the virtual object's position and movements to the movements as recognized by Object and Gesture Recognition System, the Object and Velocity and Direction Module would capture the dynamics of the virtual object's movements, and the Virtual Object Behavior Module would receive the input from the Object and Velocity and Direction Module to generate data that would direct the movements of the virtual object to correspond to the input from the Object and Velocity and Direction Module.

The Virtual Object Tracker Module 606 on the other hand may be adapted to track where a virtual object should be located in three-dimensional space in a vicinity of a display, and which body part of the user is holding the virtual object, based on input from the Object and Gesture Recognition Module. The Virtual Object Tracker Module 606 may for example track a virtual object as it moves across and between screens and track which body part of the user is holding that virtual object. Tracking the body part that is holding the virtual object allows a continuous awareness of the body part's air movements, and thus an eventual awareness as to whether the virtual object has been released onto one or more screens.

The Gesture to View and Screen Synchronization Module 608, receives the selection of the view and screen or both from the Direction of Attention Module 623 and, in some cases, voice commands to determine which view is the active view and which screen is the active screen. It then causes the relevant gesture library to be loaded for the Object and Gesture Recognition System 622. Various views of an application on one or more screens can be associated with alternative gesture libraries or a set of gesture templates for a given view. As an example in FIG. 1A a pinch-release gesture launches a torpedo, but in FIG. 1B, the same gesture launches a depth charge.

The Adjacent Screen Perspective Module 607, which may include or be coupled to the Device Proximity Detection Module 625, may be adapted to determine an angle and position of one display relative to another display. A projected display includes, for example, an image projected onto a wall or screen. The ability to detect a proximity of a nearby screen and a corresponding angle or orientation of a display projected therefrom may for example be accomplished with either an infrared emitter and receiver, or electromagnetic or photo-detection sensing capability. For technologies that allow projected displays with touch input, the incoming video can be analyzed to determine the position of a projected display and to correct for the distortion caused by displaying at an angle. An accelerometer, magnetometer, compass, or camera can be used to determine the angle at which a device is being held while infrared emitters and cameras could allow the orientation of the screen device to be determined in relation to the sensors on an adjacent device. The Adjacent Screen Perspective Module 607 may, in this way, determine coordinates of an adjacent screen relative to its own screen coordinates. Thus, the Adjacent Screen Perspective Module may determine which devices are in proximity to each other, and further potential targets for moving one or more virtual object's across screens. The Adjacent Screen Perspective Module may further allow the position of the screens to be correlated to a model of three-dimensional space representing all of the existing objects and virtual objects.

The Object and Velocity and Direction Module 603 may be adapted to estimate the dynamics of a virtual object being moved, such as its trajectory, velocity (whether linear or angular), momentum (whether linear or angular), etc. by receiving input from the Virtual Object Tracker Module. The Object and Velocity and Direction Module may further be adapted to estimate dynamics of any physics forces, by for example estimating the acceleration, deflection, degree of stretching of a virtual binding, etc. and the dynamic behavior of a virtual object once released by a user's body part. The Object and Velocity and Direction Module may also use image motion, size and angle changes to estimate the velocity of objects, such as the velocity of hands and fingers The Momentum and Inertia Module 602 can use image motion, image size, and angle changes of objects in the image plane or in a three-dimensional space to estimate the velocity and direction of objects in the space or on a display.

The Momentum and Inertia Module is coupled to the Object and Gesture Recognition System 622 to estimate the velocity of gestures performed by hands, fingers, and other body parts and then to apply those estimates to determine momentum and velocities to virtual objects that are to be affected by the gesture.

The 3D Image Interaction and Effects Module 605 tracks user interaction with 3D images that appear to extend out of one or more screens. The influence of objects in the z-axis (towards and away from the plane of the screen) can be calculated together with the relative influence of these objects upon each other. For example, an object thrown by a user gesture can be influenced by 3D objects in the foreground before the virtual object arrives at the plane of the screen. These objects may change the direction or velocity of the projectile or destroy it entirely. The object can be rendered by the 3D Image Interaction and Effects Module in the foreground on one or more of the displays.

The following clauses and/or examples pertain to further embodiments or examples. Specifics in the examples may be used anywhere in one or more embodiments. The various features of the different embodiments or examples may be variously combined with some features included and others excluded to suit a variety of different applications. Examples may include subject matter such as a method, means for performing acts of the method, at least one machine-readable medium including instructions that, when performed by a machine cause the machine to performs acts of the method, or of an apparatus or system for facilitating hybrid communication according to embodiments and examples described herein.

Some embodiments pertain to Example 1 that includes an apparatus to facilitate smart monitoring of body dimensions, comprising: detection/reception logic to receive a first request to take a first picture of a user, wherein the first picture is taken at a first point in time using a depth-sensing camera; analysis/model computation logic to automatically compute first body dimensions relating to a body of the user based on at least one of a first image of the body and first depth information relating to one or more parts of the body, wherein the first image and the first depth information are obtained from the first picture, wherein the analysis/model computation logic is further to generate a first three-dimensional (3D) model of the body based on the first body dimensions; and communication/compatibility logic to communicate at least one of the first 3D model and the first body dimensions to a display device, wherein the display device to display at least one of the first 3D model and the first body dimensions.

Example 2 includes the subject matter of Example 1, wherein the detection/reception logic is further to receive a second request to take second picture of the user, wherein the second picture is taken at a second point in time using the depth-sensing camera, wherein the analysis/model computation logic is further to automatically compute second body dimensions relating to the body of the user based on at least one of a second image of the body and second depth information relating to the one or more parts of the body, wherein the second image and the second depth information are obtained from the second picture, wherein the analysis/model computation logic is further to generate a second 3D model of the body based on the second body dimensions.

Example 3 includes the subject matter of Example 1, further comprising target dimensions logic to analyze target body dimensions relating to the body of the user, wherein the target body dimensions are received from the user and indicate the user's anticipated dimensions of the body, wherein the analysis/model computation logic is further to generate a target 3D model of the body based on the target body dimensions.

Example 4 includes the subject matter of Example 1, further comprising tracking/comparing logic to monitor one or more of the first 3D model, the second 3D model, and the target 3D model to detect one or more differences between at least two or more of the first body dimensions, the second body dimensions, and the target body dimensions associated with the first 3D model, the second 3D model, and the target 3D model, respectively, wherein the one or more differences are indicative of one or more changes relating to the one or more parts of the body.

Example 5 includes the subject matter of Example 1 or 4, further comprising recommendation/prediction logic to predict attaining or missing of the target 3D model based on the one or more changes, wherein the one or more changes reflect progress or lack of progress relating to the one or more parts of the body towards the target 3D model.

Example 6 includes the subject matter of Example 5, wherein the recommendation/prediction logic is further to offer one or more recommendations to the user based on the progress or the lack of progress, wherein the one or more recommendations include at least one of a new plan and modifications to or termination of an existing plan, wherein the new and existing plans include or are based on one or more of workout plans, diet plans, dedicated time periods, equipment, and personnel.

Example 7 includes the subject matter of Example 1, further comprising stitching/merging logic to compare the first image with the second image, wherein the stitching/merging logic is further to merge the first image with the second image to generate a stitched image for simultaneous viewing of the first body dimensions and the second body dimensions at the first period of time and the second period of time, respectively, wherein the stitched image is displayed at the display device.

Example 8 includes the subject matter of Example 1, further comprising privacy logic to encrypt contents of at least one of the first image, the second image, the stitched image, the first 3D model, the second 3D model, and the target 3D model, wherein the encryption of the contents ensures privacy of the contents during transmission or displaying of the contents such that the user's body or other private data remains secured.

Example 9 includes the subject matter of Example 1, further comprising user interface logic to facilitate a user interface for communication of the contents, wherein one or more of the first request, the second request, and the target body dimensions are placed via the user interface.

Some embodiments pertain to Example 10 that includes a method for facilitating smart monitoring of body dimensions, comprising: receiving a first request to take a first picture of a user, wherein the first picture is taken at a first point in time using a depth-sensing camera; automatically computing first body dimensions relating to a body of the user based on at least one of a first image of the body and first depth information relating to one or more parts of the body, wherein the first image and the first depth information are obtained from the first picture; generating a first three-dimensional (3D) model of the body based on the first body dimensions; and communicating at least one of the first 3D model and the first body dimensions to a display device, wherein the display device to display at least one of the first 3D model and the first body dimensions.

Example 11 includes the subject matter of Example 10, further comprising: receiving a second request to take second picture of the user, wherein the second picture is taken at a second point in time using the depth-sensing camera; and automatically computing second body dimensions relating to the body of the user based on at least one of a second image of the body and second depth information relating to the one or more parts of the body, wherein the second image and the second depth information are obtained from the second picture; and generating a second 3D model of the body based on the second body dimensions.

Example 12 includes the subject matter of Example 10, further comprising: analyzing target body dimensions relating to the body of the user, wherein the target body dimensions are received from the user and indicate the user's anticipated dimensions of the body; and generating a target 3D model of the body based on the target body dimensions.

Example 13 includes the subject matter of Example 10, further comprising monitoring one or more of the first 3D model, the second 3D model, and the target 3D model to detect one or more differences between at least two or more of the first body dimensions, the second body dimensions, and the target body dimensions associated with the first 3D model, the second 3D model, and the target 3D model, respectively, wherein the one or more differences are indicative of one or more changes relating to the one or more parts of the body.

Example 14 includes the subject matter of Example 10 or 13, further comprising predicting attaining or missing of the target 3D model based on the one or more changes, wherein the one or more changes reflect progress or lack of progress relating to the one or more parts of the body towards the target 3D model.

Example 15 includes the subject matter of Example 14, further comprising offering one or more recommendations to the user based on the progress or the lack of progress, wherein the one or more recommendations include at least one of a new plan and modifications to or termination of an existing plan, wherein the new and existing plans include or are based on one or more of workout plans, diet plans, dedicated time periods, equipment, and personnel.

Example 16 includes the subject matter of Example 10, further comprising: comparing the first image with the second image; and merging the first image with the second image to generate a stitched image for simultaneous viewing of the first body dimensions and the second body dimensions at the first period of time and the second period of time, respectively, wherein the stitched image is displayed at the display device.

Example 17 includes the subject matter of Example 10, further comprising encrypting contents of at least one of the first image, the second image, the stitched image, the first 3D model, the second 3D model, and the target 3D model, wherein the encryption of the contents ensures privacy of the contents during transmission or displaying of the contents such that the user's body or other private data remains secured.

Example 18 includes the subject matter of Example 10, further comprising facilitating a user interface for communication of the contents, wherein one or more of the first request, the second request, and the target body dimensions are placed via the user interface.

Some embodiments pertain to Example 19 includes a system comprising a storage device having instructions, and a processor to execute the instructions to facilitate a mechanism to: receive a first request to take a first picture of a user, wherein the first picture is taken at a first point in time using a depth-sensing camera; automatically compute first body dimensions relating to a body of the user based on at least one of a first image of the body and first depth information relating to one or more parts of the body, wherein the first image and the first depth information are obtained from the first picture; generate a first three-dimensional (3D) model of the body based on the first body dimensions; and communicate at least one of the first 3D model and the first body dimensions to a display device, wherein the display device to display at least one of the first 3D model and the first body dimensions.

Example 20 includes the subject matter of Example 19, wherein the mechanism is further to: receive a second request to take second picture of the user, wherein the second picture is taken at a second point in time using the depth-sensing camera; automatically compute second body dimensions relating to the body of the user based on at least one of a second image of the body and second depth information relating to the one or more parts of the body, wherein the second image and the second depth information are obtained from the second picture; and generate a second 3D model of the body based on the second body dimensions.

Example 21 includes the subject matter of Example 19, wherein the mechanism is further to: analyze target body dimensions relating to the body of the user, wherein the target body dimensions are received from the user and indicate the user's anticipated dimensions of the body; and generate a target 3D model of the body based on the target body dimensions.

Example 22 includes the subject matter of Example 19, wherein the mechanism is further to monitor one or more of the first 3D model, the second 3D model, and the target 3D model to detect one or more differences between at least two or more of the first body dimensions, the second body dimensions, and the target body dimensions associated with the first 3D model, the second 3D model, and the target 3D model, respectively, wherein the one or more differences are indicative of one or more changes relating to the one or more parts of the body.

Example 23 includes the subject matter of Example 19 or 22, wherein the mechanism is further to predict attaining or missing of the target 3D model based on the one or more changes, wherein the one or more changes reflect progress or lack of progress relating to the one or more parts of the body towards the target 3D model.

Example 24 includes the subject matter of Example 23, wherein the mechanism is further to offer one or more recommendations to the user based on the progress or the lack of progress, wherein the one or more recommendations include at least one of a new plan and modifications to or termination of an existing plan, wherein the new and existing plans include or are based on one or more of workout plans, diet plans, dedicated time periods, equipment, and personnel.

Example 25 includes the subject matter of Example 19, wherein the mechanism is further to: compare the first image with the second image; and merge the first image with the second image to generate a stitched image for simultaneous viewing of the first body dimensions and the second body dimensions at the first period of time and the second period of time, respectively, wherein the stitched image is displayed at the display device.

Example 26 includes the subject matter of Example 19, wherein the mechanism is further to encrypt contents of at least one of the first image, the second image, the stitched image, the first 3D model, the second 3D model, and the target 3D model, wherein the encryption of the contents ensures privacy of the contents during transmission or displaying of the contents such that the user's body or other private data remains secured.

Example 27 includes the subject matter of Example 19, wherein the mechanism is further to facilitate a user interface for communication of the contents, wherein one or more of the first request, the second request, and the target body dimensions are placed via the user interface.

Some embodiments pertain to Example 28 includes an apparatus comprising: means for receiving a first request to take a first picture of a user, wherein the first picture is taken at a first point in time using a depth-sensing camera; means for automatically computing first body dimensions relating to a body of the user based on at least one of a first image of the body and first depth information relating to one or more parts of the body, wherein the first image and the first depth information are obtained from the first picture; means for generating a first three-dimensional (3D) model of the body based on the first body dimensions; and means for communicating at least one of the first 3D model and the first body dimensions to a display device, wherein the display device to display at least one of the first 3D model and the first body dimensions.

Example 29 includes the subject matter of Example 28, further comprising: means for receiving a second request to take second picture of the user, wherein the second picture is taken at a second point in time using the depth-sensing camera; means for automatically computing second body dimensions relating to the body of the user based on at least one of a second image of the body and second depth information relating to the one or more parts of the body, wherein the second image and the second depth information are obtained from the second picture; and generating a second 3D model of the body based on the second body dimensions.

Example 30 includes the subject matter of Example 28, further comprising: means for analyzing target body dimensions relating to the body of the user, wherein the target body dimensions are received from the user and indicate the user's anticipated dimensions of the body; and means for generating a target 3D model of the body based on the target body dimensions.

Example 31 includes the subject matter of Example 28, further comprising means for monitoring one or more of the first 3D model, the second 3D model, and the target 3D model to detect one or more differences between at least two or more of the first body dimensions, the second body dimensions, and the target body dimensions associated with the first 3D model, the second 3D model, and the target 3D model, respectively, wherein the one or more differences are indicative of one or more changes relating to the one or more parts of the body.

Example 32 includes the subject matter of Example 28 or 31, further comprising means for predicting attaining or missing of the target 3D model based on the one or more changes, wherein the one or more changes reflect progress or lack of progress relating to the one or more parts of the body towards the target 3D model.

Example 33 includes the subject matter of Example 32, further comprising means for offering one or more recommendations to the user based on the progress or the lack of progress, wherein the one or more recommendations include at least one of a new plan and modifications to or termination of an existing plan, wherein the new and existing plans include or are based on one or more of workout plans, diet plans, dedicated time periods, equipment, and personnel.

Example 34 includes the subject matter of Example 28, further comprising: means for comparing the first image with the second image; and means for merging the first image with the second image to generate a stitched image for simultaneous viewing of the first body dimensions and the second body dimensions at the first period of time and the second period of time, respectively, wherein the stitched image is displayed at the display device.

Example 35 includes the subject matter of Example 28, further comprising means for encrypting contents of at least one of the first image, the second image, the stitched image, the first 3D model, the second 3D model, and the target 3D model, wherein the encryption of the contents ensures privacy of the contents during transmission or displaying of the contents such that the user's body or other private data remains secured.

Example 36 includes the subject matter of Example 28, further comprising means for facilitating a user interface for communication of the contents, wherein one or more of the first request, the second request, and the target body dimensions are placed via the user interface.

Example 37 includes at least one non-transitory or tangible machine-readable medium comprising a plurality of instructions, when executed on a computing device, to implement or perform a method as claimed in any of claims or examples 10-18.

Example 38 includes at least one machine-readable medium comprising a plurality of instructions, when executed on a computing device, to implement or perform a method as claimed in any of claims or examples 10-18.

Example 39 includes a system comprising a mechanism to implement or perform a method as claimed in any of claims or examples 10-18.

Example 40 includes an apparatus comprising means for performing a method as claimed in any of claims or examples 10-18.

Example 41 includes a computing device arranged to implement or perform a method as claimed in any of claims or examples 10-18.

Example 42 includes a communications device arranged to implement or perform a method as claimed in any of claims or examples 10-18.

Example 43 includes at least one machine-readable medium comprising a plurality of instructions, when executed on a computing device, to implement or perform a method or realize an apparatus as claimed in any preceding claims or examples.

Example 44 includes at least one non-transitory or tangible machine-readable medium comprising a plurality of instructions, when executed on a computing device, to implement or perform a method or realize an apparatus as claimed in any preceding claims or examples.

Example 45 includes a system comprising a mechanism to implement or perform a method or realize an apparatus as claimed in any preceding claims or examples.

Example 46 includes an apparatus comprising means to perform a method as claimed in any preceding claims or examples.

Example 47 includes a computing device arranged to implement or perform a method or realize an apparatus as claimed in any preceding claims or examples.

Example 48 includes a communications device arranged to implement or perform a method or realize an apparatus as claimed in any preceding claims or examples.

The drawings and the forgoing description give examples of embodiments. Those skilled in the art will appreciate that one or more of the described elements may well be combined into a single functional element. Alternatively, certain elements may be split into multiple functional elements. Elements from one embodiment may be added to another embodiment. For example, orders of processes described herein may be changed and are not limited to the manner described herein. Moreover, the actions of any flow diagram need not be implemented in the order shown; nor do all of the acts necessarily need to be performed. Also, those acts that are not dependent on other acts may be performed in parallel with the other acts. The scope of embodiments is by no means limited by these specific examples. Numerous variations, whether explicitly given in the specification or not, such as differences in structure, dimension, and use of material, are possible. The scope of embodiments is at least as broad as given by the following claims.

What is claimed is:

1. An apparatus comprising:
    a depth sensing camera;
    a processor coupled to the depth sensing camera, the processor configured to perform a detection/reception logic to receive any one of a first and second request to cause the depth sensing camera to take a respective first and second picture of a user, wherein the first picture is taken at a first point in time and the second picture is taken at a second point in time;
    the processor further configured to perform analysis/model computation logic to compute:
    first body dimensions relating to a body of the user based on at least one of a first image of the body and first depth information relating to one or more parts of the body, wherein the first image and the first depth information are obtained from the first picture, wherein the analysis/model computation logic is further to cause the processor to generate a first three-dimensional (3D) model of the body based on the first body dimensions, and
    second body dimensions relating to the body of the user based on at least one of a second image of the body and second depth information relating to the one or more parts of the body, wherein the second image and the second depth information are obtained from the second picture, wherein the analysis/model computation logic is further to cause the processor to generate a second 3D model of the body based on the second body dimensions;
    the processor further configured to perform stitching/merging logic to:
    merge the first image with the second image to generate a single stitched image that is reflective of any changes in the users' body dimensions from the first point in time to the second point in time;
    merge the first 3D model with the second 3D model to generate a single stitched 3D model that is reflective of any changes in the users' body dimensions from the first point in time to the second point in time; and
    a display device coupled to the processor, the processor further configured to perform communication/compatibility logic to communicate at least one of the stitched image, the first and second images, the stitched 3D model, the first and second 3D models, and the first and second body dimensions to the display device, wherein the display device is to display any two or more of the stitched, first and second images and stitched, first and second 3D models simultaneously to reflect any changes in the users' body dimensions from the first point in time to the second point in time.

2. The apparatus of claim 1, the processor further configured to perform target dimensions logic to analyze target body dimensions relating to the body of the user, wherein the target body dimensions are received from the user and indicate the user's anticipated dimensions of the body,
    wherein the analysis/model computation logic is further to cause the processor to generate a target 3D model of the body based on the target body dimensions.

3. The apparatus of claim 2, the processor further configured to perform tracking/comparing logic to monitor one or more of the first 3D model, the second 3D model, and the target 3D model to detect one or more differences between at least two or more of the first body dimensions, the second body dimensions, and the target body dimensions associated with the first 3D model, the second 3D model, and the target 3D model, respectively, wherein the one or more differences are indicative of one or more changes relating to the one or more parts of the body.

4. The apparatus of claim 3, the processor further configured to perform recommendation/prediction logic to predict attaining or missing of the target 3D model based on the one or more changes, wherein the one or more changes reflect progress or lack of progress relating to the one or more parts of the body towards the target 3D model.

5. The apparatus of claim 4, wherein the recommendation/prediction logic is further to cause the processor to display one or more recommendations to the user based on the progress or the lack of progress, wherein the one or more displayed recommendations include at least one of a new plan and modifications to or termination of an existing plan, wherein the new and existing plans include or are based on one or more of workout plans, diet plans, dedicated time periods, equipment, and personnel.

6. The apparatus of claim 4, the processor further configured to perform a privacy logic to encrypt contents of at least one of the first image, the second image, the stitched image, the first 3D model, the second 3D model, and the target 3D model, wherein the encryption of the contents ensures privacy of the contents during transmission or displaying of the contents such that the images and models of the user's body or other private data remains secured.

7. The apparatus of claim 6, the processor further configured to perform a user interface logic to facilitate a user interface for communication of the contents, wherein one or more of the first request, the second request, and the target body dimensions are received via the user interface.

8. A method comprising:
    receiving, in a processor coupled to a depth-sensing camera and a display device, any one of a first and second request to take a respective first and second picture of a user, wherein the first picture is taken at a first point in time and the second picture is taken at a second point in time;
    performing in the processor:
    computing first body dimensions relating to a body of the user based on at least one of a first image of the body and first depth information relating to one or more parts of the body, wherein the first image and the first depth information are obtained from the first picture,
    computing second body dimensions relating to the body of the user based on at least one of a second image of the body and second depth information relating to the one or more parts of the body, wherein the second image and the second depth information are obtained from the second picture;

generating a first and second three-dimensional (3D) model of the body based on the respective first and second body dimensions;

merging the first image with the second image to generate a single stitched image that is reflective of any changes in the users' body dimensions from the first point in time to the second point in time;

merging the first 3D model with the second 3D model to generate a single stitched 3D model that is reflective of any changes in the users' body dimensions from the first point in time to the second point in time; and displaying simultaneously on the display device any two or more of the stitched image and the first and second images, the stitched 3D model and the first and second 3D models, and the first and second body dimensions, wherein the displaying of the images and models reflects any changes in the user's body dimensions from the first point in time to the second point in time.

9. The method of claim 8, further comprising:
performing in the processor:
analyzing target body dimensions relating to the body of the user, wherein the target body dimensions are received from the user and indicate the user's anticipated dimensions of the body; and
generating a target 3D model of the body based on the target body dimensions.

10. The method of claim 9, further comprising:
performing in the processor:
monitoring one or more of the first 3D model, the second 3D model, and the target 3D model to detect one or more differences between at least two or more of the first body dimensions, the second body dimensions, and the target body dimensions associated with the first 3D model, the second 3D model, and the target 3D model, respectively, wherein the one or more differences are indicative of one or more changes relating to the one or more parts of the body.

11. The method of claim 10, further comprising:
performing in the processor, predicting attaining or missing of the target 3D model based on the one or more changes, wherein the one or more changes reflect progress or lack of progress relating to the one or more parts of the body towards the target 3D model.

12. The method of claim 11, further comprising:
displaying on the display device one or more recommendations to the user based on the progress or the lack of progress, wherein the one or more recommendations include at least one of a new plan and modifications to or termination of an existing plan, wherein the new and existing plans include or are based on one or more of workout plans, diet plans, dedicated time periods, equipment, and personnel.

13. The method of claim 9, further comprising:
performing in the processor, encrypting contents of at least one of the first image, the second image, the stitched image, the first 3D model, the second 3D model, and the target 3D model, wherein the encryption of the contents ensures privacy of the contents during transmission or displaying of the contents such that the images and models of the user's body or other private data remains secured.

14. The method of claim 13, further comprising displaying a user interface for communication of the contents, wherein one or more of the first request, the second request, and the target body dimensions are received via the user interface.

15. At least one non-transitory machine-readable storage medium comprising a plurality of instructions stored thereon, the instructions when executed on a computing device, cause the computing device to:
receive any one of a first and second request to cause a depth-sensing camera to take a respective first and second picture of a user, wherein the first picture is taken at a first point in time and the second picture is taken at a second point in time;
compute first body dimensions relating to a body of the user based on at least one of a first image of the body and first depth information relating to one or more parts of the body, wherein the first image and the first depth information are obtained from the first picture;
compute second body dimensions relating to the body of the user based on at least one of a second image of the body and second depth information relating to the one or more parts of the body, wherein the second image and the second depth information are obtained from the second picture;
generate a first and second three-dimensional (3D) model of the body based on the respective first and second body dimensions;
merge the first image with the second image to generate a single stitched image that is reflective of any changes in the users' body dimensions from the first point in time to the second point in time;
merge the first 3D model with the second 3D model to generate a single stitched 3D model that is reflective of any changes in the users' body dimensions from the first point in time to the second point in time, and
cause the display device to simultaneously display any two or more of the stitched image and the first and second images, the stitched 3D model and the first and second 3D models, and the first and second body dimensions, the simultaneous display reflecting any changes in the user's body dimensions from the first point in time to the second point in time.

16. The at least one non-transitory machine-readable storage medium of claim 15, wherein the instructions, when executed, further cause the computing device to:
analyze target body dimensions relating to the body of the user, wherein the target body dimensions are received from the user and indicate the user's anticipated dimensions of the body; and
generate a target 3D model of the body based on the target body dimensions.

17. The at least one non-transitory machine-readable storage medium of claim 16, wherein the instructions, when executed, cause the computing device to monitor one or more of the first 3D model, the second 3D model, and the target 3D model to detect one or more differences between at least two or more of the first body dimensions, the second body dimensions, and the target body dimensions associated with the first 3D model, the second 3D model, and the target 3D model, respectively, wherein the one or more differences are indicative of one or more changes relating to the one or more parts of the body.

18. The at least one non-transitory machine-readable storage medium of claim 17, wherein the instructions, when executed, cause the computing device to predict attaining or missing of the target 3D model based on the one or more changes, wherein the one or more changes reflect progress or lack of progress relating to the one or more parts of the body towards the target 3D model.

19. The at least one non-transitory machine-readable storage medium of claim 18, wherein the instructions, when executed, further cause the computing device to display one or more recommendations to the user based on the progress or the lack of progress, wherein the one or more recommendations include at least one of a new plan and modifications to or termination of an existing plan, wherein the new and existing plans include or are based on one or more of workout plans, diet plans, dedicated time periods, equipment, and personnel.

* * * * *